US008715958B2

(12) United States Patent
Goerke et al.

(10) Patent No.: US 8,715,958 B2
(45) Date of Patent: May 6, 2014

(54) CELL-FREE SYNTHESIS OF PROTEINS CONTAINING UNNATURAL AMINO ACIDS

(75) Inventors: Aaron R. Goerke, Stanford, CA (US); James Robert Swartz, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/305,617

(22) PCT Filed: Jun. 29, 2007

(86) PCT No.: PCT/US2007/015170
§ 371 (c)(1),
(2), (4) Date: Nov. 25, 2009

(87) PCT Pub. No.: WO2008/066583
PCT Pub. Date: Jun. 5, 2008

(65) Prior Publication Data
US 2010/0093024 A1 Apr. 15, 2010

Related U.S. Application Data

(60) Provisional application No. 60/817,772, filed on Jun. 29, 2006, provisional application No. 60/817,915, filed on Jun. 29, 2006.

(51) Int. Cl.
*C12P 21/00* (2006.01)
*C07K 2/00* (2006.01)

(52) U.S. Cl.
USPC ......... 435/68.1; 435/193; 435/69.1; 435/194; 530/402; 506/9

(58) Field of Classification Search
None
See application file for complete search history.

(56) References Cited

U.S. PATENT DOCUMENTS

| 6,337,191 | B1 | 1/2002 | Swartz et al. | |
|---|---|---|---|---|
| 7,045,337 | B2 | 5/2006 | Schultz et al. | |
| 7,338,789 | B2 * | 3/2008 | Swartz et al. | 435/71.2 |
| 2004/0209321 | A1 | 10/2004 | Swartz et al. | |
| 2005/0054032 | A1 | 3/2005 | Voloshin et al. | |
| 2005/0054044 | A1 | 3/2005 | Swartz et al. | |

FOREIGN PATENT DOCUMENTS

| JP | 2004261160 | 9/2004 |
|---|---|---|
| JP | 2005536206 | 12/2005 |
| WO | 2004/016778 | 2/2004 |
| WO | 2004016778 | 2/2004 |
| WO | 2005/052117 | 6/2005 |

OTHER PUBLICATIONS

Ibba et al. (Relaxing the substrate specificity of an aminoacyl-tRNA synthetase allows in vitro and in vivo synthesis of proteins containing unnatural amino acids FEBS Letters vol. 364 (3) May 15, 1995, pp. 272-275.*
Calhoun; et al., "Energizing Cell-Free Protein Synthesis with Glucose Metabolism", Biotechnology and Bioengineering (2005), 90(5):606-13.
Chin; et al., "Addition of p-Azido-L-phenylalanine to the Genetic Code of *Escherichia coli*", J. Am. Chem. Soc. (2002), 124:9026-9027.
Cornish; et al., "Probing Protein Structure and Function with an Expanded Genetic Code", Angew. Chem. Int. Ed. Engl. (1995), 34:621-633.
Farrell; et al., "Photo-cross-linking interacting proteins with a genetically encoded benzophenone", Nature Methods (2005), 2(5):377-8.
Jewett; et al., "Prokaryotic Systems for In Vitro Expression", Gene Cloning and Expression Technologies (2002), p. 391-411.
Jewett; et al., "Mimicking the *Escherichia coli* Cytoplasmic Environment Activates Long-Lived and Efficient Cell-Free Protein Synthesis", Biotechnology and Bioengineering (2004), 86(1):19-26.
Lin; et al., "Genetic Reconstruction of the Aerobic Central Metabolism in *Escherichia coli* for the Absolute Aerobic Production of Succinate", Biotechnology and Bioengineering (2004), 89(2):148-56.
Liu; et al., "A Method for the Generation of Glycoprotein Mimetics", J. Am. Chem. Soc. (2003), 125:1702-1703.
Noren; et al., "A General Method for Site-Specific Incorporation of Unnatural Amino Acids into Proteins", Science (1989), 244(4902):182-188.
Wang; et al., "Addition of the keto functional group to the genetic code of *Escherichia coli*", PNAS (2003), 100 (1):56-61.
Wang; et al., "Expanding the Genetic Code of *Escherichia coli*", Science (2001), 292(5516):498-500.
Ali; et al. "Improvements in the cell-free production of functional antibodies using cell extract from protease-deficient *Escherichia coli* mutant", J Biosci Bioeng (Feb. 2005), 99(2):181-186.
Jiang; et al. "Reduction of protein degradation by use of protease-deficient mutants in cell-free protein synthesis system of *Escherichia coli*", J Biosci Bioeng (2002), 93(3):151-156.
Klammt; et al. "High level cell-free expression and specific labeling of integral membrane proteins", Eur J Biochem (Feb. 2004), 271(3):568-580.
Kohrer; et al. "Use of T7 RNA polymerase in an optimized *Escherichia coli* coupled in vitro transcription-translation system. Application in regulatory studies and expression of long transcription units", Eur J Biochem (Feb. 1996), 236 (1):234-239.
Spirin; et al. "A continuous cell-free translation system capable of producing polypeptides in high yield", Science (Nov. 1988), 242(4882):1162-1164.

* cited by examiner

*Primary Examiner* — Kagnew H Gebreyesus
(74) *Attorney, Agent, or Firm* — Bozicevic, Field & Francis LLP; Pamela J. Sherwood

(57) ABSTRACT

Methods are provided for the utilization of bacterial cell-free extracts in the synthesis of polypeptides containing unnatural amino acids at one or more specified residues of the polypeptide.

16 Claims, 8 Drawing Sheets

Band 1: o-Synthetase Product
Band 2: Modified Protein Product
Band 3: Truncated mGM-CSF Product $^1$ O-Syn. produced in KC6 cell extract
$^2$ O-Syn. produced in ARG1, ARG2, or MCJ29

CELL-FREE SYNTHESIS OF PROTEINS CONTAINING UNNATURAL AMINO ACIDS

BACKGROUND OF THE INVENTION

Protein synthesis is a fundamental biological process that underlies the development of polypeptide therapeutics, vaccines, diagnostics, and industrial enzymes. With the advent of recombinant DNA (rDNA) technology, it has become possible to harness the catalytic machinery of the cell to produce a desired protein. This can be achieved within the cellular environment or in vitro using extracts derived from cells.

Cell-free protein synthesis offers several advantages over in vivo protein expression methods. Cell-free systems can direct most, if not all, of the metabolic resources of the cell towards the exclusive production of one protein. Moreover, the lack of a cell wall in vitro is advantageous since it allows for control of the synthesis environment. For example, tRNA levels can be changed to reflect the codon usage of genes being expressed. The redox potential, pH, or ionic strength can also be altered with greater flexibility than in vivo since we are not concerned about cell growth or viability. Furthermore, direct recovery of purified, properly folded protein products can be easily achieved.

In vitro translation is also recognized for its ability to incorporate unnatural and isotope-labeled amino acids as well as its capability to produce proteins that are unstable, insoluble, or cytotoxic in vivo. In addition, cell-free protein synthesis may play a role in revolutionizing protein engineering and proteomic screening technologies. The cell-free method bypasses the laborious processes required for cloning and transforming cells for the expression of new gene products in vivo, and is becoming a platform technology for this field.

RELEVANT LITERATURE

U.S. Pat. No. 7,045,337, issued May 16, 2006, herein specifically incorporated by reference.

U.S. Pat. No. 6,337,191 B1; Swartz et al. U.S. Patent Published Application 2004/0209321; Swartz et al. International Published Application WO 2004/016778; Swartz et al. U.S. Patent Published Application 2005-0054032-A1; Swartz et al. U.S. Patent Published Application 2005-0054044-A1; Swartz et al. International Published Application WO 2005/052117. Calhoun and Swartz (2005) Biotechnol Bioeng 90(5):606-13; Jewett and Swartz (2004) Biotechnol Bioeng 86(1):19-26; Jewett et al. (2002) Prokaryotic Systems for In Vitro Expression. In: Weiner M, Lu Q, editors. Gene cloning and expression technologies. Westborough, Mass.: Eaton Publishing. p 391-411; Lin et al. (2005) Biotechnol Bioeng 89(2):148-56. (Wang et al. (2001) Science 292(5516):498-500; Wang et al. (2003) Proc Natl Acad Sci USA 100(1):56-61; Chin et al. (2002) J Am Chem Soc 124(31):9026-7; Farrell et al. (2005) Nat Methods, 2005. 2(5):377-84; Liu et al. (2003) J Am Chem Soc 125(7):1702-3.

SUMMARY OF THE INVENTION

Methods are provided for high yield cell-free protein synthesis with bacterial cell extracts from a polynucleotide template, where the synthesized protein is modified to comprise one or more site-specifically incorporated unnatural amino acids. The protein is synthesized in a cell-free reaction mixture comprising at least one orthogonal tRNA aminoacylated with an unnatural amino acid, where the orthogonal tRNA base pairs with a codon that is not normally associated with an amino acid, e.g. a stop codon; a 4 by codon, etc. The reaction mixture also comprises a tRNA synthetase capable of aminoacylating the orthogonal tRNA with an unnatural amino acid. Usually the orthogonal tRNA synthetase, which is susceptible to degradation by proteases present in bacterial cell extracts, is exogenously synthesized and added to the reaction mix prior to initiation of polypeptide synthesis. The orthogonal tRNA may be synthesized in the bacterial cells from which the cell extract is obtained, may be synthesized de novo during the polypeptide synthesis reaction, or may be exogenously added to the reaction mix.

The methods of the invention provide for high yields of active, modified protein. Proteins thus produced, including proteins containing disulfide bonds, secreted proteins, membrane-bound proteins, multimeric proteins, etc., are biologically active. In some embodiments the synthesis is performed as a coupled transcription and translation reaction.

In one embodiment, the synthesis reaction conditions provide for in vitro activation of oxidative phosphorylation. The activation of oxidative phosphorylation may be evidenced by sensitivity of synthesis to electron transport chain inhibitors. Such reactions are substantially free of polyethylene glycol.

The cell-free protein synthesis system provides a flexible platform for expressing proteins containing unnatural amino acids. In various embodiments, the system is modified to achieve a specific result. The number and nature of the unnatural amino acid is varied according to the desired modification. Various sources are used for the orthogonal tRNA and tRNA synthetase, including bacterial, archaebacterial, or mammalian species.

Components that affect unnatural amino acid insertion and protein insertion or folding are optionally added to the reaction mixture. Such components include elevated concentrations of translation factors to minimize the effect of release factor 1 and 2 and to further optimize orthogonal component concentrations. Protein chaperones (Dsb System of oxidoreductases and isomerases, GroES, GroEL, DNAJ, DNAK, Skp, etc.) may be exogenously added to the reaction mixture or may be overexpressed in the source cells used to prepare the cell extract.

Modified protein production after a 5 hour cell-free reaction at 30° C. following controlled tRNA transcription in the cell extract (example derived from the KC6 cell strain) and with increasing amounts of orthogonal synthetase added. (B, C) Autoradiography time course and active CAT yields during cell-free protein synthesis in the unAA-PANOx-SP system. Approximately 167 µg/mL of orthogonal p-azido-phenylalanine synthetase was used in the 22 hour cell-free reaction conducted at 30° C.

Figure 4:
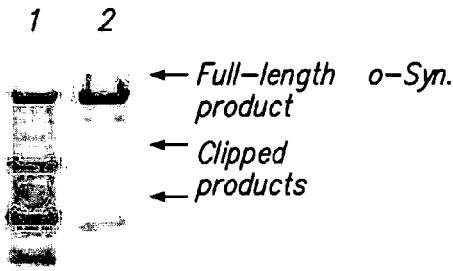

FIG. 4. Autoradiography analysis of orthogonal synthetase accumulation after expression in a cell-free protein synthesis reaction. The autoradiogram was developed from a 10% Bis-Tris NuPAGE gel run in MES buffer. The p-azido-phenylalanine tRNA synthetase is severely degraded by proteases in the KC6 cell extract. The synthetase is not degraded when the ARG1, ARG2, or the MCJ29 mutant cell strains are used to produce the cell-extracts (a single example is given since all results were similar). When the ompT deletion or mutation is incorporated into KC6 or KGK10 cell strains, the newly produced synthetase is stable.

Figure 5:
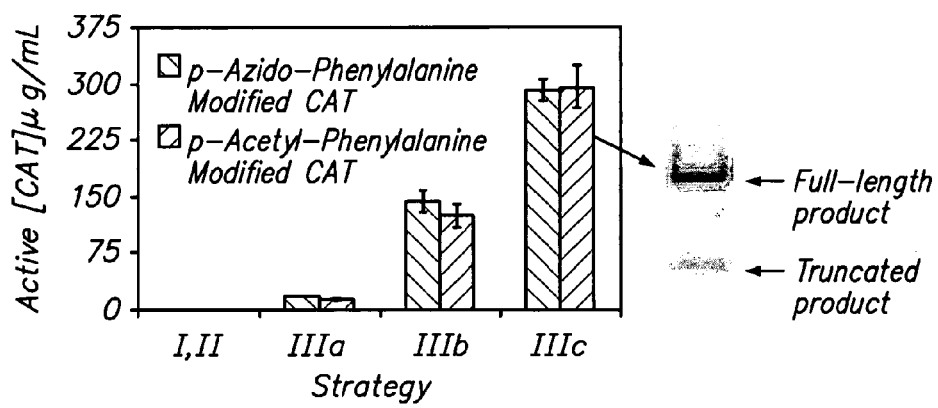

FIG. 5. The yields of active chloramphenicol acetyl transferase (CAT) from reactions employing reaction strategies I to IIIc show the dramatic improvements provided by this invention. Developmental phases I and II involve incorporation of purified tRNA and synthetase in physiological amounts (yields were similar to those described in Example 1). Developmental strategy IIIa involves expression of orthogonal synthetase and tRNA in vivo (KC6 cell extract). Developmental strategy IIIb involves transcription of tRNA in vivo and the addition of less than 167 µg/mL of active, purified orthogonal synthetase. Development strategy IIIc resulted from improvements in unAA-PANOx-SP component ratios, the reaction environment, and the extract preparation protocol and the tRNA expression. Analysis of protein products via autoradiography shows that the majority of the cell-free reaction product is full-length protein containing an unnatural amino acid. These results were reproduced in greater than n=6 experiments.

Figure 6:
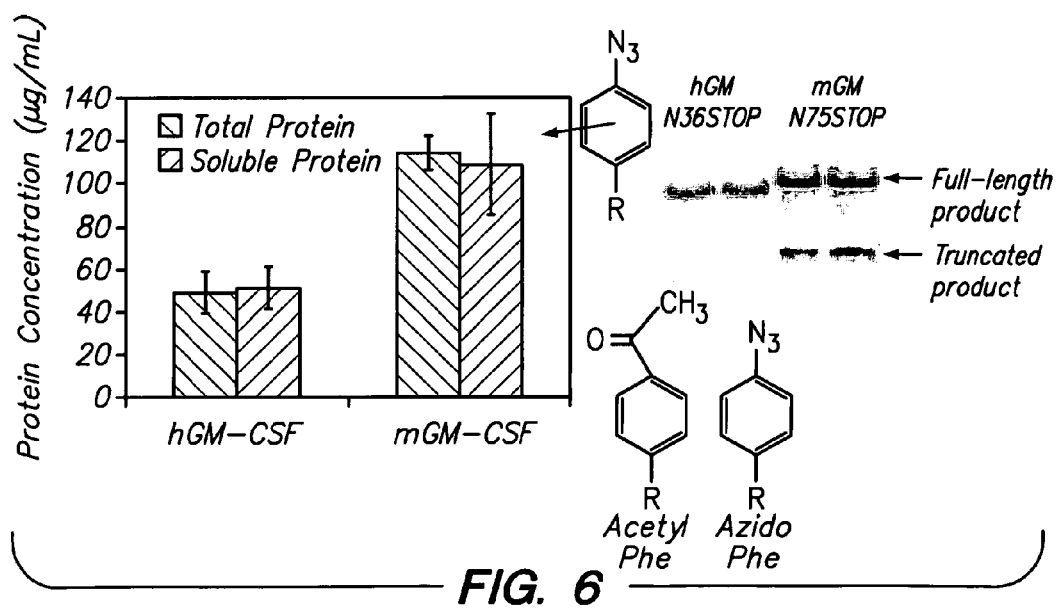

FIG. 6. Modified protein production of disulfide bond containing proteins. The p-azido and p-acetyl-phenylalanine unnatural amino acids were successfully incorporated into hGM-CSF and mGM-CSF (only p-azido-phenylalanine cell-free yields are shown). The autoradiogram for both p-acetyl-phenylalanine and p-azido-phenylalanine incorporation confirms that full length modified product is synthesized by the new unAA-PANOx-SP cell-free system. The KC6 cell strain containing the pK7tRNAmj plasmid was used to make the cell extract. For each unnatural amino acid and protein, three separate cell-free reactions were conducted at 30° C. for 6 hours.

Figure 7:
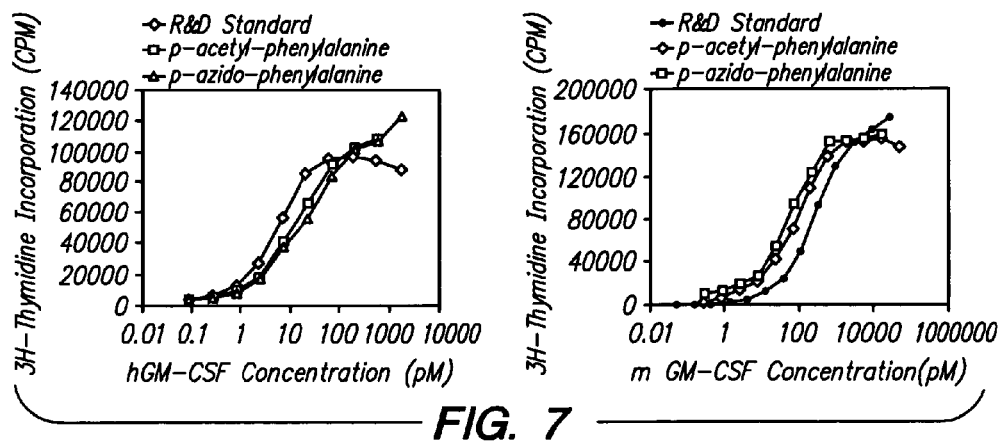

FIG. 7. Bioactivity assay results for hGM-CSF and mGM-CSF for the modified protein products described in FIG. 6. Nearly all of the full length product (soluble fraction) that is produced is correctly folded and displays bioactivity when tested within the cell proliferation based assay. Samples were tested in triplicate (n=3).

FIG. 8. Autoradiogram analysis of the cell-free production of full length TetA membrane protein with an unAA (p-azido-phenylalanine) incorporated at residue 34 or 182. Also shown is the distribution of TetA protein products separated by a sucrose gradient floatation assay. The synthesized TetA protein was identified by its radioactivity after 14C-leucine incorporation. Vesicle-associated TetA floats up to fraction 2, while aggregated TetA remains at the bottom of the gradient in fractions 5-7. The glutamate phosphate cell-free system was used to synthesize these membrane proteins ensuring an active oxidative phosphorylation pathway.

Figure 9:
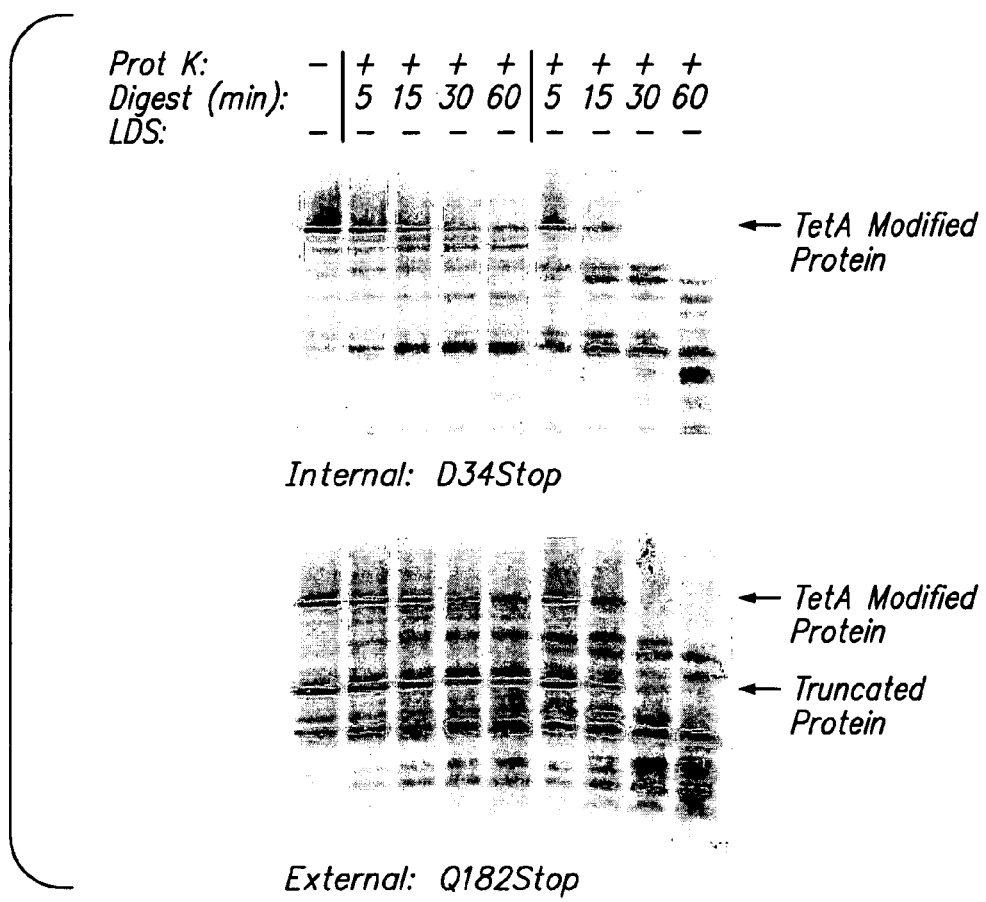

FIG. 9. Autoradiography analysis of protease K digestion of TetA that has been modified with p-azido-phenylalanine at residues 34 and 182. A 10% Bis-Tris NuPAGE gel in MES buffer was used for this experiment. The "internal" unnatural amino acid substitution is on the periplasmic side of the membrane (inside the vesicle) and the "external" inserted unnatural amino acid is on the cytoplasmic side of the membrane (outside the vesicle).

Figure 10:
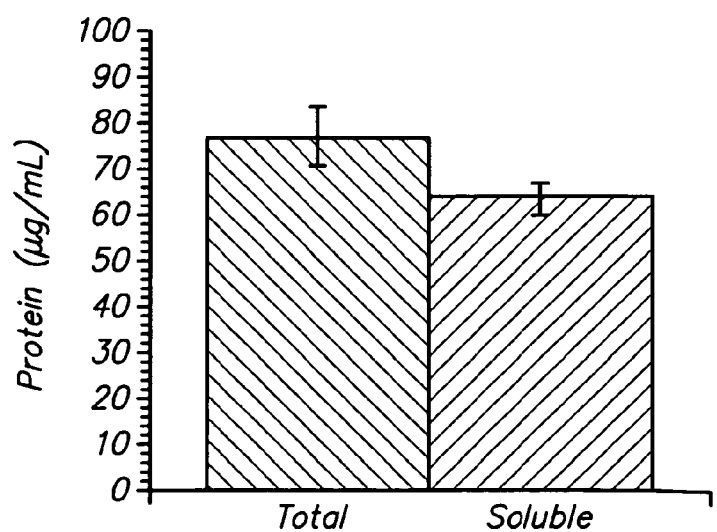

FIG. 10: Cell-free protein synthesis yield using pET24a_MS2 cp_T15STOP expression vector (30 µl reactions, n=2).

Figure 11:
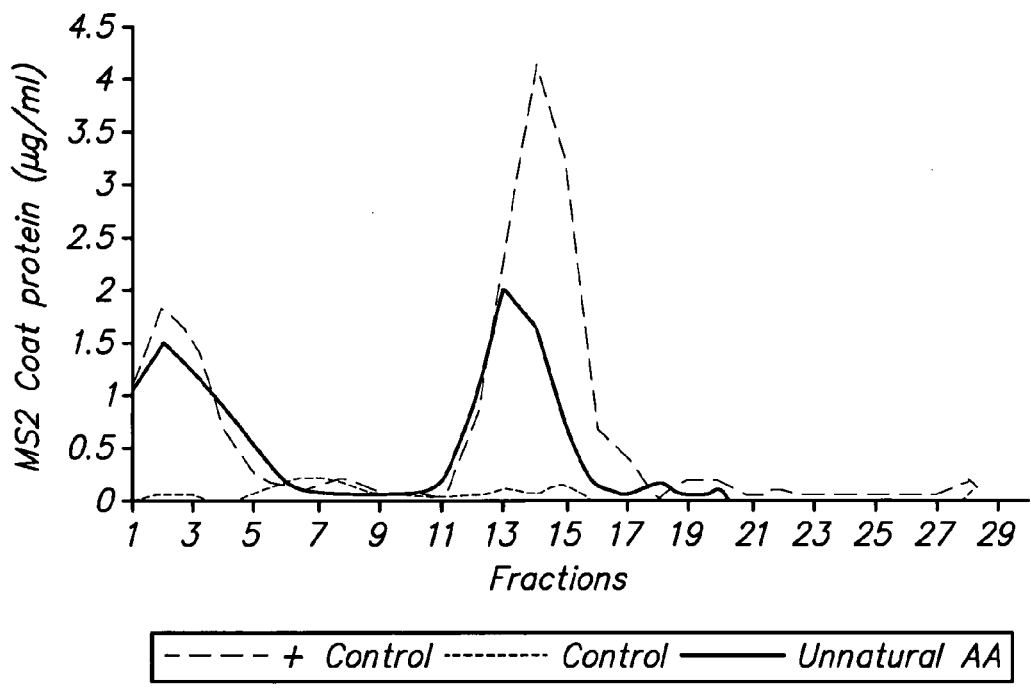

FIG. 11: The 10%-40% (with 2.5% steps) sucrose density gradient velocity sedimentation profile of MS2 capsid samples synthesized with natural amino acids (+control) and with stop codon suppression by p-azido-phenylalanine at position 15 (unnatural AA). The location of radiolabeled MS2 coat protein is determined by scintillation counting of incorporated $^{14}$C-leucine.

Figure 12:
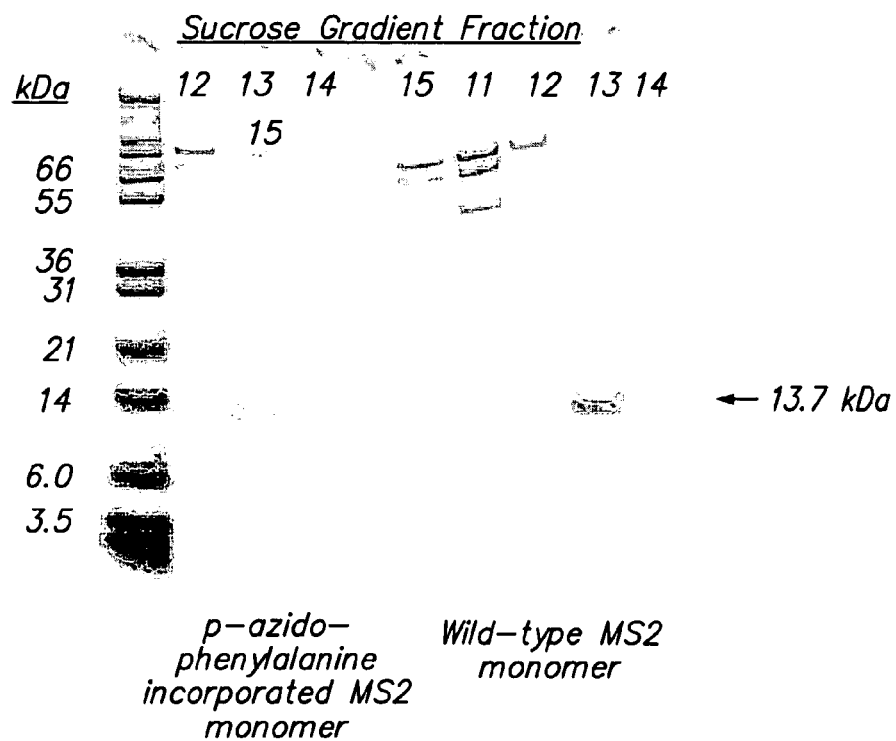

FIG. 12: SDS-Page Gel (10% Bis-Tris Gel w/MES running buffer, Invitrogen; 60 min at 60 mA running conditions; SimplySafe Stain, Invitrogen) of fractions 12 through 15 of the unnatural amino acid sample separated by the sucrose density gradient shown in FIG. 11 and fractions 11 through 15 of the +control sample (20 µl of fraction, 7.25 µl NuPAGE LDS Sample Buffer-Invitrogen, 0.625 mM DTT-Invitrogen). The MS2 coat protein monomer molecular weight is 13.7 kDa.

Figure 13:
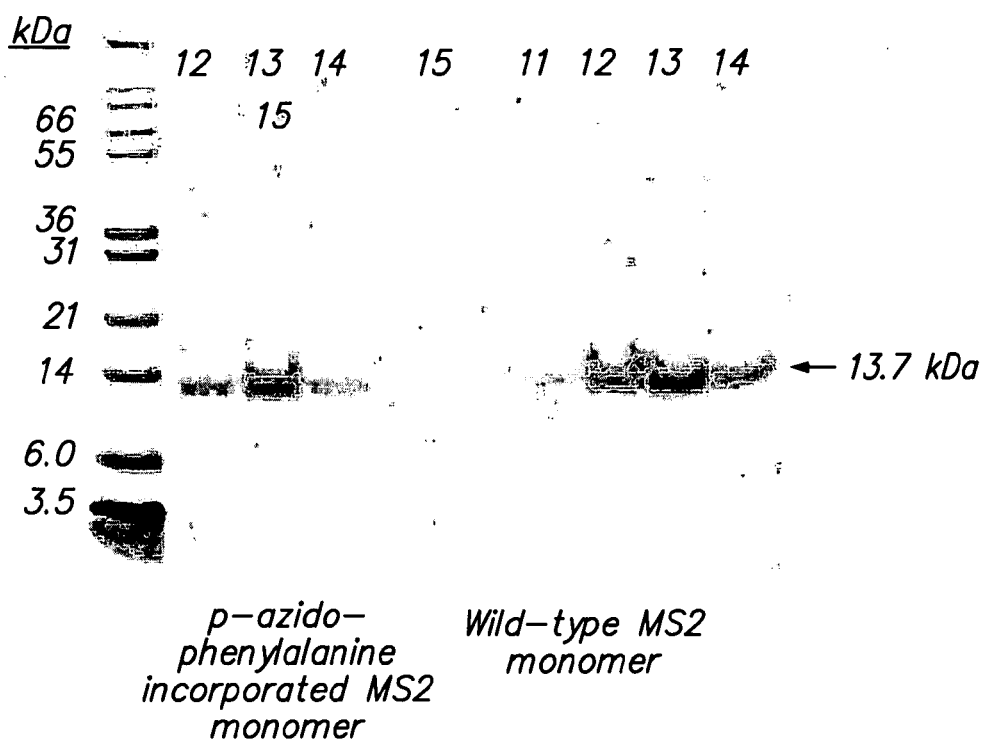
Figure 14A:
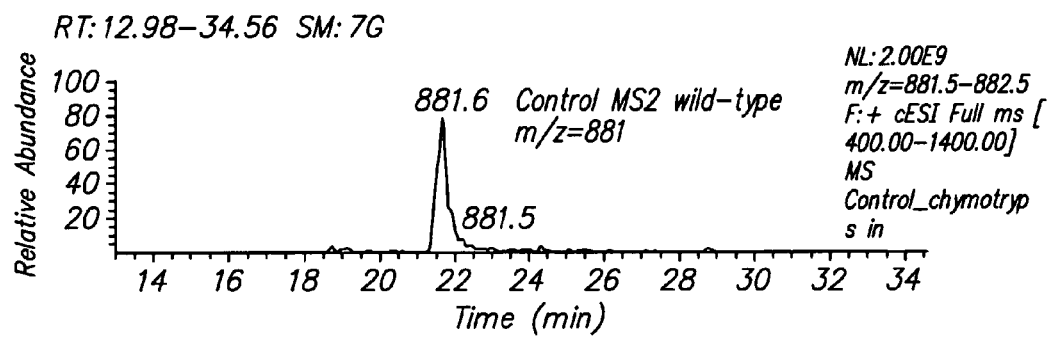
Figure 14B:
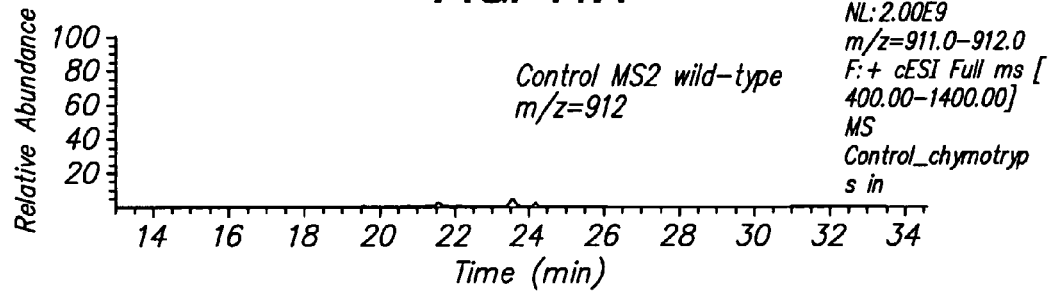
Figure 14C:
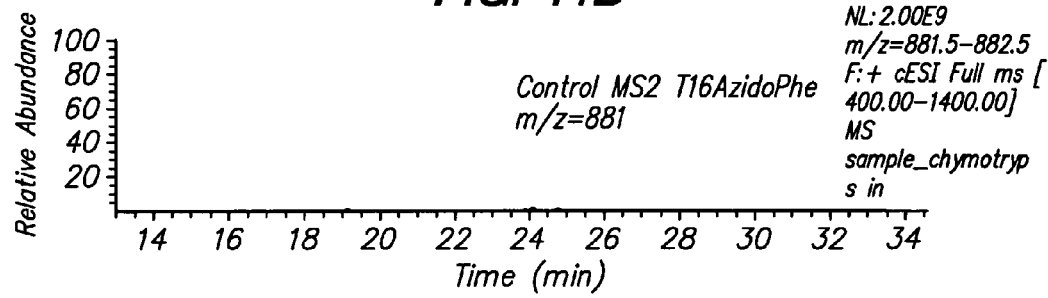
Figure 14D:
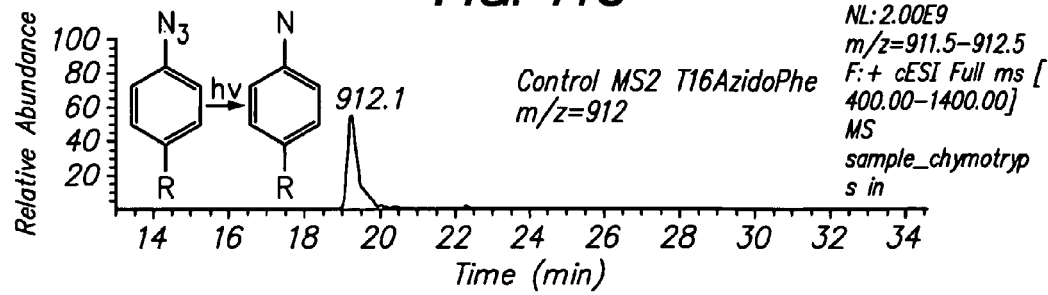

FIG. 13: Autoradiogram of gel shown in FIG. 12.

FIGS. 14A-D: Mass spectroscopy analysis of the relevant chymotrypsin fragment of the MS2 coat protein isolated from VLPs synthesized with p-azido-phenylalanine or with tyrosine at position 15 The control and p-azido-phenylalanine products were first isolated and then were digested with chymotrypsin.

DETAILED DESCRIPTION OF THE EMBODIMENTS

In the methods of the invention, a target protein is synthesized in a cell-free reaction mixture comprising at least one orthogonal tRNA aminoacylated with an unnatural amino acid, where the orthogonal tRNA base pairs with a nonsense codon that is not normally associated with an amino acid, e.g. a stop codon; a 4 by codon, etc. Included in the methods are coupled transcription-translation reactions. The invention uses nonsense codon suppression during cell-free protein synthesis to produce high yields of polypeptides containing unnatural amino acids. Polypeptides of interest include, without limitation, proteins containing disulfide bonds, any heterogenous or homogeneous combination of proteins, including fusion proteins, viral coat proteins, and/or proteins originally secreted through or within a cellular membrane. Unnatural amino acids constitute any amino acid analog or similar entity that is not commonly found in nature, including but not limited to those molecules that can be used for targeted post-translational modification. The reaction mixture comprises cell extracts, which are optionally amino acid stabilized, reductase minimized, and/or protease mutated cell extracts.

It has been surprisingly found that although orthogonal tRNA can be reliably synthesized by the bacterial cells from which an extract for cell-free synthesis is made, the orthogonal tRNA synthetase is susceptible to degradation in the bacterial cell extracts. At least one factor in this degradation is the presence of the ompT protease in the bacterial cell. This protease does not normally contact polypeptides within the cytoplasm of the cell, and therefore does not adversely affect orthogonal components during synthesis of polypeptides with unnatural amino acids in intact cells. In the methods of the invention, tRNA synthetase is exogenously synthesized and added to the cell-free reaction mix. Alternatively, the reaction mix is prepared from bacterial cells in which ompT has been inactivated or is naturally inactive.

The methods of the invention provide for high yields of active, modified protein, which may be greater than the yield that can be achieved with in vivo expression systems. In one embodiment of the invention, the yield of active modified protein is at least about 50 µg/ml of reaction mixture; at least about 100 µg/ml of reaction mixture; at least about 250 µg/ml of reaction mixture; or more. A substantial portion of the target polypeptide thus produced contains the desired unnatural amino acid, usually at least about 50%, at least about 75%, at least about 85%, at least about 95%, at least about 99%, or higher.

A modified protein, or target protein, as used herein, comprises at least one unnatural amino acid at a pre-determined site, and may comprise or contain 1, 2, 3, 4, 5 or more unnatural amino acids. If present at two or more sites in the polypeptide, the unnatural amino acids can be the same or different. Where the unnatural amino acids are different, an orthogonal tRNA and cognate tRNA synthetase will be present for each unnatural amino acid. Unnatural amino acids include, without limitation, p-acetyl-phenylalanine, p-ethynyl-phenylalanine, p-propargyloxyphenylalanine, and p-azido-phenylalanine.

The methods of the present invention provide for proteins containing unnatural amino acids that have biological activity comparable to the native protein. One may determine the specific activity of a protein in a composition by determining the level of activity in a functional assay, quantitating the amount of protein present in a non-functional assay, e.g. immunostaining, ELISA, quantitation on coomasie or silver stained gel, etc., and determining the ratio of biologically active protein to total protein. Generally, the specific activity as thus defined will be at least about 5% that of the native protein, usually at least about 10% that of the native protein, and may be about 25%, about 50%, about 90% or greater.

The methods of the invention provide for high yields of self-assembling viral coat proteins. A substantial portion of the protein is may be assembled into stable virus like particles (VLP), usually at least about 25%, at least about 50%, at least about 75% or more, where a stable VLP maintains a capsid structure comprising at least about 60 polypeptide chains under physiological conditions for extended periods of time, e.g. for at least about 24 hrs, at least about 1 week, at least about 1 month, or more. Once assembled, the VLP can have a stability commensurate with the native virus particle, e.g. upon exposure to pH changes, heat, freezing, ionic changes, etc.

The polypeptides synthesized by the methods of the invention provide the benefits of being able to attach any ligand (containing or not containing disulfide bonds) to the polypeptide through unnatural amino acids covalently bonding to other unnatural amino acids. Linkers may be used to link two similar or unique unnatural amino acids, e.g. between two polypeptide chains. Site-specific post-translational modification at single or multiple sites using similar or different ligands may be conducted by but not limited by mild [3+2] cycloaddition reactions or ligand specific reactivity using a unique "ketone handle". Alternatively, an azido group can be linked to an alkyne where either is incorporated into the polypeptide surface and the other is part of a linker or ligand.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The terms "desired protein" or "selected protein" are used interchangeably and refer generally to any peptide or protein having more than about 5 amino acids, which comprises at least one unnatural amino acid, which unnatural amino acid is encoded at a specific site in a protein coding polynucleotide. The polypeptides may be homologous to, or may be exogenous, meaning that they are heterologous, i.e., foreign, to the bacteria from which the bacterial cell-free extract is derived, such as a human protein, viral protein, yeast protein, etc. produced in the bacterial cell-free extract.

Examples of mammalian polypeptides include, but are not limited to, molecules such as renin; growth hormones, including human growth hormone; bovine growth hormone; growth hormone releasing factor; parathyroid hormone; thyroid stimulating hormone; lipoproteins; alpha-1-antitrypsin; insulin A-chain; insulin; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES and other chemokines; human macrophage inflammatory protein (MIP-1α); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-18; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

Virus coat proteins of interest include any of the known virus type, e.g. dsDNA viruses, such as smallpox (variola);

vaccinia; herpesviruses including varicella-zoster; HSV1, HSV2, KSVH, CMV, EBV; adenovirus; hepatitis B virus; SV40; T even phages such as T4 phage, T2 phage; lambda phage; etc. Single stranded DNA viruses include phiX-174; adeno-associated virus, etc. Negative-stranded RNA viruses include measles virus; mumps virus; respiratory syncytial virus (RSV); parainfluenza viruses (PIV); metapneumovirus; rabies virus; Ebola virus; influenza virus; etc. Positive-stranded RNA viruses include polioviruses; rhinoviruses; coronaviruses; rubella; yellow fever virus; West Nile virus; dengue fever viruses; equine encephalitis viruses; hepatitis A and hepatitis C viruses; tobacco mosaic virus (TMV); etc. Double-stranded RNA viruses include reovirus; etc. Retroviruses include rous sarcoma virus; lentivirus such as HIV-1 and HIV-2; etc.

Bacteriophage are of interest, e.g. the MS2 bacteriophage. Myoviridae (phages with contractile tails) include mu-like viruses; P1-like viruses, e.g. P1; phiW39, etc.; P2-like viruses; SPO-1-like viruses; T4-like viruses; etc. Podoviridae (phages with short tails) include N4-like viruses; P22-like viruses, e.g. P22; phi-29-like viruses, e.g. phi-29; T7-like viruses, e.g. T3; T7; W31; etc. Siphoviridae (phages with long non-contractile tails) include c2-like viruses; L5-like viruses; Lambda-like viruses, e.g. phage lambda, HK022; HK97, etc.; N15-like viruses; PhiC31-like viruses; psiM1-like viruses; T1-like viruses, e.g. phage T1, etc. Microviridae (isometric ssDNA phages) include Chlamydiamicrovirus; Microvirus, e.g. phage alpha 3, phage WA13, etc.; phage G4; phage phiX174 and related coliphages. Many additional phages known to those of skill in the art remain unclassified. The sequence of many coat proteins are publicly available.

Unnatural amino acids. Examples of unnatural amino acids that can be used in the methods of the invention include: an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; a cyclic amino acid other than proline, etc.

Unnatural amino acids of interest include, without limitation, amino acids that provide a reactant group for CLICK chemistry reactions (see *Click Chemistry: Diverse Chemical Function from a Few Good Reactions* Hartmuth C. Kolb, M. G. Finn, K. Barry Sharpless Angewandte Chemie International Edition Volume 40, 2001, P. 2004, herein specifically incorporated by reference). For example, the amino acids p-acetyl-L-phenylalanine and p-azido-L-phenylalanine are of interest.

Orthogonal components. As used herein, orthogonal components include a tRNA aminoacylated with an unnatural amino acid, where the orthogonal tRNA base pairs with a codon that is not normally associated with an amino acid, e.g. a stop codon; a 4 by codon, etc. The reaction mixture may further comprise a tRNA synthetase capable of aminoacylating (with an unnatural amino acid) the cognate orthogonal tRNA. Such components are known in the art, for example as described in U.S. Pat. No. 7,045,337, issued May 16, 2006. The orthogonal tRNA recognizes a selector codon, which may be nonsense codons, such as, stop codons, e.g., amber, ochre, and opal codons; four or more base codons; codons derived from natural or unnatural base pairs and the like. The orthogonal tRNA anticodon loop recognizes the selector codon on the mRNA and incorporates the unnatural amino acid at this site in the polypeptide.

Orthogonal tRNA synthetase is preferably synthesized exogenously, purified and added to the reaction mix of the invention, usually in a defined quantity, of at least about 10 μg/ml, at least about 20 μg/ml, at least about 30 μg/ml, and not more than about 200 μg/ml. The protein may be synthesized in bacterial or eukaryotic cells and purified, e.g. by affinity chromatography, PAGE, gel exclusion chromatography, reverse phase chromatography, and the like, as known in the art.

The orthogonal tRNA may be synthesized in the cells from which the extract for cell-free synthesis is obtained; may be exogenously synthesized, purified and added to the reaction mix, or may be synthesized de novo, where the cell-free synthesis reaction allows for transcription and translation reactions. Where the orthogonal tRNA is synthesized in the cells from which the extract for cell-free synthesis is obtained, the expression may be controlled through appropriate selection of promoters, medium, and the like.

In vitro synthesis, as used herein, refers to the cell-free synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art.

In some embodiments of the invention, cell free synthesis is performed in a reaction where oxidative phosphorylation is activated, e.g. the CYTOMIM™ system. The activation of the respiratory chain and oxidative phosphorylation is evidenced by an increase of polypeptide synthesis in the presence of $O_2$. In reactions where oxidative phosphorylation is activated, the overall polypeptide synthesis in presence of $O_2$ is reduced by at least about 40% in the presence of a specific electron transport chain inhibitor, such as HQNO, or in the absence of $O_2$. The reaction chemistry may be as described in international patent application WO 2004/016778, herein incorporated by reference.

The CYTOMIM™ environment for synthesis utilizes cell extracts derived from bacterial cells grown in medium containing glucose and phosphate, where the glucose is present initially at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as *E. coli*, using both defined and undefined sources of nutrients (see Sambrook, J., E. F. Fritsch, and T. Maniatis. 1989. Molecular Cloning: A Laboratory Manual, $2^{nd}$ edition. Cold Spring Harbor University Press, Cold Spring Harbor, N.Y. for examples of glucose containing media). Alternatively, the culture may be grown using a protocol in which the glucose is continually fed as required to maintain a high growth rate in either a defined or complex growth medium.

The reaction mixture may be supplemented by the inclusion of vesicles, e.g. an inner membrane vesicle solution. Where provided, such vesicles may comprise from about 0 to about 0.5 volumes, usually from about 0.1 to about 0.4 volumes.

In some embodiments, PEG will be present in not more than trace amounts, for example less than 0.1%, and may be less than 0.01%. Reactions that are substantially free of PEG contain sufficiently low levels of PEG that, for example, oxidative phosphorylation is not PEG-inhibited. The molecules spermidine and putrescine may be used in the place of PEG. Spermine or spermidine is present at a concentration of at least about 0.5 mM, usually at least about 1 mM, preferably about 1.5 mM, and not more than about 2.5 mM. Putrescine is present at a concentration of at least about 0.5 mM, preferably at least about 1 mM, preferably about 1.5 mM, and not more than about 2.5 mM. The spermidine and/or putrescine may be present in the initial cell extract or may be separately added.

The concentration of magnesium in the reaction mixture affects the overall synthesis. Often there is magnesium present in the cell extracts, which may then be adjusted with additional magnesium to optimize the concentration. Sources of magnesium salts useful in such methods are known in the art. In one embodiment of the invention, the source of magnesium is magnesium glutamate. A preferred concentration of magnesium is at least about 5 mM, usually at least about 10 mM, and preferably a least about 12 mM; and at a concentration of not more than about 25 mM, usually not more than about 20 mM. Other changes that may enhance synthesis or reduce cost include the omission of HEPES buffer and phosphoenol pyruvate from the reaction mixture.

The system can be run under aerobic and anaerobic conditions. Oxygen may be supplied, particularly for reactions larger than 15 µl, in order to increase synthesis yields. The headspace of the reaction chamber can be filled with oxygen; oxygen may be infused into the reaction mixture; etc. Oxygen can be supplied continuously or the headspace of the reaction chamber can be refilled during the course of protein expression for longer reaction times. Other electron acceptors, such as nitrate, sulfate, or fumarate may also be supplied in conjunction with preparing cell extracts so that the required enzymes are active in the cell extract.

It is not necessary to add exogenous cofactors for activation of oxidative phosphorylation. Compounds such as nicotinamide adenine dinucleotide (NADH), NAD$^+$, or acetyl-coenzyme A may be used to supplement protein synthesis yields but are not required. Addition of oxalic acid, a metabolic inhibitor of phosphoenolpyruvate synthetase (Pps), may be beneficial in increasing protein yields, but is not necessary.

The template for cell-free protein synthesis can be either mRNA or DNA, preferably a combined system continuously generates mRNA from a DNA template with a recognizable promoter. Either an endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally present at a concentration of at least about 50 mM, and not more than about 250 mM. Ammonium may be present, usually at a concentration of not more than 200 mM, more usually at a concentration of not more than about 100 mM. Usually, the reaction is maintained in the range of about pH 5-10 and a temperature of about 20°-50° C.; more usually, in the range of about pH 6-9 and a temperature of about 25°-40° C. These ranges may be extended for specific conditions of interest.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Biological extracts. For the purposes of this invention, biological extracts are any preparation comprising the components required for protein synthesis machinery, usually a bacterial cell extract, wherein such components are capable of expressing a nucleic acid encoding a desired protein. Thus, a bacterial extract comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, $N^{10}$-formyltetrahydrofolate, formylmethionine-tRNAf$^{Met}$ synthetase, peptidyl transferase, initiation factors such as IF-1, IF-2 and IF-3, elongation factors such as EF-Tu, EF-Ts, and EF-G, release factors such as RF-1, RF-2, and RF-3, and the like.

In a preferred embodiment of the invention, the reaction mixture comprises extracts from bacterial cells, e.g. *E. coli* S30 extracts, as is known in the art. In some embodiments the bacterial strain is modified such that it endogenously expresses an orthogonal tRNA. For convenience, the organism used as a source of extracts may be referred to as the source organism. Methods for producing active extracts are known in the art, for example they may be found in Pratt (1984), Coupled transcription-translation in prokaryotic cell-free systems, p. 179-209, in Hames, B. D. and Higgins, S. J. (ed.), Transcription and Translation: A Practical Approach, IRL Press, New York. Kudlicki et al. (1992) Anal Biochem 206(2):389-93 modify the S30 *E. coli* cell-free extract by collecting the ribosome fraction from the S30 by ultracentrifugation. Zawada and Swartz Biotechnol Bioeng, 2006. 94(4): p. 618-24 and Liu et al., 2005, Biotechnol Progr 21:460 teach a modified procedure for extract preparation.

The bacterial strain from which the extract is derived may be further modified for the purposes of the invention. In one embodiment, the extract is derived from an *E. coli* strain deficient in one or more proteins, e.g. strain KC6 (A19ΔtonAΔtnaAΔspeAΔendAΔsdaAΔsdaBΔgshA met$^+$), KGK10 (A19ΔspeAΔtnaAΔtonAΔendAΔsdaAΔsdaBΔgshAΔgor met$^+$ which can include TrxB-HA, ARG1 (A19ΔtonAΔtnaAΔspeAΔendAΔsdaAΔsdaBΔgshA met$^+$ OmpTD83A), ARG2 (A19ΔtonAΔtnaAΔtonAΔendAΔsdaAΔsdaBΔgshAΔgor met$^+$ OmpTD83A which can include TrxB-HA); MCJ29 (A19ΔspeAΔtnaAΔompTΔptrCΔdegPΔtonAΔendA met$^+$) and the like.

Folding, as used herein, refers to the process of forming the three-dimensional structure of polypeptides and proteins, where interactions between amino acid residues act to stabilize the structure. Non-covalent interactions are important in determining structure, and the effect of membrane contacts with the protein may be important for the correct structure. For naturally occurring proteins and polypeptides or derivatives and variants thereof, the result of proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The synthesis of membrane-associated protein may be followed by direct isolation of the active, membrane associated forms, i.e. in the absence of refolding or post-translational introduction of membranes. The separation procedure may utilize conditions that maintain membrane integrity, as is known in the art or may use any of several membrane active detergents used to isolated membrane proteins as commonly practiced in the art.

Separation procedures of interest include affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural biospecific binding of one molecular species to separate and purify a second species from a mixture. Antibodies are commonly used in affinity chromatography. Preferably a microsphere or matrix is used as the support for affinity chromatography. Such supports are known in the art and are commercially available, and include activated supports that can be coupled to the linker molecules. For example, Affi-Gel supports, based on agarose or polyacrylamide are low pressure gels suitable for most laboratory-scale purifications with a peristaltic pump or gravity flow elution. Affi-Prep supports, based on a pressure-stable macroporous polymer, are suitable for preparative and process scale applications.

Proteins may also be separated by ion exchange chromatography, and/or concentrated, filtered, dialyzed, etc., using methods known in the art.

Methods for Synthesis

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

Strategies for synthesis where at least one unnatural amino acid is introduced into the polypeptide strand during elongation include but are not limited to: (I) addition of exogenous purified orthogonal synthetase, unnatural amino acid, and orthogonal tRNA to the cell-free reaction, (II) addition of exogenous purified orthogonal synthetase and unnatural amino acid to the reaction mixture, but with orthogonal tRNA transcribed during the cell-free reaction, (III) addition of exogenous purified orthogonal synthetase and unnatural amino acid to the reaction mixture, but with orthogonal tRNA synthesized by the cell extract source organism. Preferably the orthogonal components are driven by regulatable promoters, so that synthesis levels can be controlled although other measures may be used such as controlling the level of the relevant DNA templates by addition or specific digestion.

In order to prevent degradation of the orthogonal synthetase, the bacterial strain used to produce extracts may have a deleted or mutated ompT (outer membrane protein T). Where ompT is mutated, it is preferably mutated in such a way that the protease function is inactive, but the chaperone function is still present. Such extracts have decreased levels of synthetase degradation relative to an extract without such a mutation or deletion.

The reaction mixture may also be modified to maintain an oxidizing protein folding environment, for example by supplementing the reaction mix with GSSG at a concentration of from about 0.5 mM to about 10 mM, usually from about 1 mM to about 4 mM; supplementing with GSH at a concentration of from about 0.5 mM to about 10 mM, usually from about 1 mM to about 4 mM. Protein components such as 100 µg/mL DsbC or Skp may also be included. Cell extracts are optionally pretreated with iodoacetamide (IAM).

The reactions may be of any volume, either in a small scale, usually at least about 1 µl and not more than about 15 µl, or in a scaled up reaction, where the reaction volume is at least about 15 µl, usually at least about 50 µl, more usually at least about 100 µl, and may be 500 µl, 1000 µl, or greater. In most cases, individual reactions will not be more than about 10 ml, although multiple reactions can be run in parallel. However, in principle, reactions may be conducted at any scale as long as sufficient oxygen (or other electron acceptor) is supplied when needed.

In addition to the above components such as cell-free extract, genetic template, and amino acids, materials specifically required for protein synthesis may be added to the reaction. These materials include salts, folinic acid, cyclic AMP, inhibitors for protein or nucleic acid degrading enzymes, inhibitors or regulators of protein synthesis, adjusters of oxidation/reduction potential(s), non-denaturing surfactants, buffer components, spermine, spermidine, putrescine, etc.

The salts preferably include potassium, magnesium, and ammonium salts (e.g. of acetic acid or glutamic acid). One or more of such salts may have an alternative amino acid as a counter anion. There is an interdependence among ionic species for optimal concentration. These ionic species are typically optimized with regard to protein production. When changing the concentration of a particular component of the reaction medium, that of another component may be changed accordingly. For example, the concentrations of several components such as nucleotides and energy source compounds may be simultaneously adjusted in accordance with the change in those of other components. Also, the concentration levels of components in the reactor may be varied over time. The adjuster of oxidation/reduction potential may be dithiothreitol, ascorbic acid, glutathione and/or their oxidized forms.

In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation. Vesicles containing the product may also be continuously isolated, for example by affinity adsorption from the reaction mixture either in situ or in a circulation loop as the reaction fluid is pumped past the adsorption matrix.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump or by applying transmembrane pressure using other methods known in the art. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein may include a unit packed with particles coated with antibody molecules or other molecules for adsorbing the synthesized, desired protein. Preferably, the protein isolating means comprises two columns for alternating use.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^3$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Kits for the practice of the subject methods may also be provided. Such kits may include bacterial extracts for protein synthesis and site directed insertion of unnatural amino acids, e.g. containing orthogonal tRNA and/or tRNA synthetase or polynucleotides encoding the same, buffers appropriate for reactions where oxidative phosphorylation is activated, and vesicles. Kits may also include vectors for protein synthesis, including vectors for expression of SRP and SR proteins; where the vectors may comprise promoter systems useful in bacterial extracts.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

The cell-free protein synthesis reactions used as examples were the Glutamate
Phosphate/Cytomim and PANOx-SP systems. These systems were modified to efficiently incorporate an unnatural amino acid into a target protein. The unnatural amino acids o-methyl-L-tyrosine, p-acetyl-L-phenylalanine, or p-azido-L-phenylalanine were site-specifically introduced at an amber stop codon using an orthogonal tRNA$^{Tyr}$/Tyrosine-synthetase pair from *Methanococcus jannaschii*. The unnatural amino acids are commercially available and the gene sequences are described in scientific literature (Wang et al. (2001) Science 292(5516):498-500; Wang et al. (2003) Proc Natl Acad Sci USA 100(1):56-61; Chin et al. (2002) J Am Chem Soc 124(31):9026-7; Farrell et al. (2005) Nat Methods, 2005. 2(5):377-84; Liu et al. (2003) J Am Chem Soc 125(7): 1702-3, herein incorporated by reference). These unnatural amino acids were incorporated into soluble bacterial proteins, secreted mammalian proteins containing disulfide bonds, and membrane proteins. This cell-free protein synthesis platform was developed by modifying cell strains used for extract preparation, extract preparation protocols, helper protein concentrations, and cell-free reaction conditions. Target protein activity may be verified by colorimetric, cell proliferation, immunoprecipitation, and transport assays, as appropriate.

Example 1

Methods for High-Yield Expression of Complex Proteins Containing Unnatural Amino Acids Using Cell-Free Protein Synthesis The bacterial protein chloramphenicol acetyl transferase (CAT), the disulfide bonded proteins mGM-CSF and hGM-CSF, and the membrane protein TetA were synthesized using the methods of the invention. To synthesize the target proteins in high yields, the template genes were synthesized by overlapping PCR from oligonucleotides that were optimized for *E. coli* tRNA relative concentrations (preferred codons). In addition, the N-terminus of the gene sequence was optimized such that it would promote translation initiation in our cell-free system (make N-terminus A-T rich). The wild-type plasmids pK7CAT, pK7hGM-CSF, pK7hGM-CSFOPT (or Further Optimized for Rare Codons), pK7mGM-CSF, and pK7TetA, were developed by ligation of the optimized protein sequences into the pK7 vector (see attached sequence) at the NdeI and SalI restriction sites. We then conducted overlapping PCR and/or QuikChange site-directed mutagenesis to insert amber stop codons (TAG) at residues that would not significantly effect folding or are known to be native glycosylation sites. This led to the development of pK7CAT_Y109STOP (SEQ ID NO:1), pK7hGM-CSF_N36STOP (SEQ ID NO:2), pK7hGM-CSFOPT_N36STOP (SEQ ID NO:3), pK7mGM-CSF_N75STOP (SEQ ID NO:4), pK7TetA_D34STOP (SEQ ID NO:5), and pK7TetA_Q182STOP (SEQ ID NO:6). {QUESTION: are these sequences going to be included with the application? They seem to be deleted at the end} The genes were under the control of T7 promoters and terminators. The plasmids were prepared following transformation into XL1-Blue chemically competent cells and were purified using a Qiagen Plasmid Maxi Kit (Qiagen, Valencia Calif.).

The components of the glutamate phosphate/cytomim cell-free reaction used to incorporate an unnatural amino acid include 13.3 µg/mL template plasmid, 1.2 mM AMP, 0.86 mM CMP, 0.86 mM GMP, 0.86 mM UMP, 34 µg/mL folinic acid, 170.6 µg/mL *E. coli* tRNA mixture, 2 mM each of 20 natural amino acids, 0.5 to 10 mM of the unnatural amino acid, 1 to 200 µg/mL of aminoacyl synthetase, 0.33 mM nicotinamide adenine dinucleotide (NAD), 0.27 mM coenzyme A (CoA), 1 mM putrescine, 1.5 mM spermidine, 4 mM sodium oxalate, 1 mM dithiothreitol, 10 mM ammonium glutamate, 130 mM potassium glutamate, 8 mM magnesium glutamate, 10 mM potassium phosphate pH 7.2, 12 µM L-[$^{14}$C]-Leucine, 0.1 mg/mL T7 RNA polymerase, 0.01 to 0.4 volumes of *E. coli* S30 extract, and 0 to 0.41 volumes of inner membrane vesicle solution.

T7 RNA polymerase is prepared from *E. coli* strain BL21 (pAR1219) as described by Grodberg and Dunn J Bacteriol, 1988. 170(3): p. 1245-53. *E. coli* S30 extract may be prepared from any of the following strains: strain KC6 (A19ΔtonAΔtnaAΔspeAΔendAΔsdaAΔsdaBΔgshA met$^+$) (Calhoun and Swartz Biotechnol Prog, 2005. 21(4): p. 1146-53), KGK10 (A19ΔspeAΔtnaAΔtonAΔendAΔsdaAΔsdaBΔgshAΔgor met$^+$ which can include TrxB-HA, ARG1 (A19ΔtonAΔtnaAΔspeAΔendAΔsdaAΔsdaBΔgshA met$^+$ OmpTD83A), ARG2 (A19ΔspeAΔtnaAΔtonAΔendAΔsdaAΔsdaBΔgshAΔgor met$^+$ OmpTD83A which can include TrxB-HA) (genomic modification procedure is described below), and MCJ29 (A19ΔspeAΔtnaAΔompTΔptrCΔdegPΔtonAΔendA met$^+$) grown according to the procedures outlined below (Zawada and Swartz, 2006, Biotechnol and Bioeng 94:618 and prepared as described by Liu et al. Biotechnol Prog, 2005. 21(2): p. 460-5). To someone skilled in the art, any other cell strains may be constructed and used to generate cell extract that could be used in this cell-free system. Extracts were also generated with the products of the pK7tRNAmj plasmid or synthetase plasmid (pK7OMeTyr) expressed during cell growth. These plasmids were engineered with the appropriate gene sequence between a constitutive (Ipp) or controllable promoter (lac, ara, etc.) and an rrnC or T7 terminator (see pK7tRNAmj).

The unAA-PANOx-SP system was chosen as an energy system. This reaction included, 170 mM potassium glutamate, 10 mM ammonium glutamate, 0.6 mM ATP, 0.43 mM each of GTP, UTP, and CTP, 1.5 mM spermidine, 1.0 mM putrescine, 17 µg/mL folinic acid, 85.3 µg/mL *E. coli* tRNA mixture, 20 natural amino acids at 2 mM each, 0.5 to 10 mM of unnatural amino acid, 0 to 200 µg/mL of aminoacyl synthetase, 10 µM L-[U-$^{14}$C]-Leucine, 0.33 mM nicotinamide adenine dinucleotide (NAD), 0.27 mM coenzyme A (CoA), 13.3 µg/mL template plasmid, 0.1 mg/mL T7 RNA polymerase, and 0.01 to 0.40 volumes *E. coli* S30 extract. The sources of the cell extract are described above. The unAA-PANOx-SP system also includes 16 mM magnesium glutamate, 33 mM phosphoenol pyruvate, and 2.7 mM sodium oxalate.

Murine GM-CSF (mGM-CSF) and human GM-CSF (hGM-CSF) were the active proteins synthesized to demonstrate modified disulfide bonded protein production. These reactions were typically 30 µL total volume unAA-PANOx-SP reactions supplemented with 1 to 16 mM oxidized glutathione buffer (GSSG), 1 to 4 mM reduced glutathione buffer (GSH), and approximately 0 to 200 µg/mL DsbC or Skp. Additionally, cell extracts were pretreated with 0 to 2 mM iodoacetamide (IAM). The necessary DsbC and Skp were prepared by over-expression and purification from the strain BL21(DE3) (Yin and Swartz, 2004, Biotechnol Bioeng, 86:188-95). In reactions requiring iodoacetamide (IAM) treatment of the extract, a small volume of concentrated IAM was first added to the reaction vessel. A much larger volume of S30 extract was then rapidly and thoroughly mixed with the small volume of IAM. The extract was incubated with the IAM for 30 minutes at room temperature before being used in the cell-free reaction.

Combined transcription-translation reactions were carried out in 1.5 mL Eppendorf tubes or petri dishes at 25 to 37° C. for 3 to 24 hours as noted.

Strategies for incorporating an unnatural acid include but are not limited to: (I) addition of purified orthogonal synthetase and orthogonal tRNA to the cell-free reaction, (II) addition of purified orthogonal synthetase, but with orthogonal tRNA transcribed during the cell-free reaction, (III) generation of cell extract from cells expressing orthogonal synthetase and/or orthogonal tRNA (with addition to the cell-free reaction of the purified factor that was not expressed in the cell extract, if any), and (IV) development of a sequential protein expression methodology.

Example 2

Purified Synthetase and Purified/Controlled tRNA Transcription in the Cell-Free Reaction Unnatural amino acid incorporation Strategies I and II are described by this example. Strategy I was the addition of purified orthogonal synthetase and purified orthogonal tRNA to the cell-free reaction, and Strategy II was the addition of purified orthogonal synthetase to the cell-free reaction mixture, but with orthogonal tRNA transcribed during the cell-free reaction.

For strategy I, in vitro transcription of the tRNA was performed from linear templates.

For a 1 mL reaction this required: 200 µL of 5× transcription buffer (200 mM Tris-HCl pH 7.9, 100 mM DTT, 125 mM MgCl$_2$), 80 or 160 µL of NTP (25 mM of each NTP) mix, 10 µL 24 µM of $^3$H UTP, 50 µL of about 0.1 mg/ml PCR-produced, purified linear DNA template (behind a T7 promoter and purified from a QIAquick PCR purification kit), 25 µL of 40 U/ml RNase out, 580 or 505 µl of water, 10 µL of 1 U/ml pyrophosphatase, 20 µL of 100 mM spermidine, and 20 µL of 5 mg/ml T7 RNA polymerase. This reaction mixture was incubated at 37° C. for 3 to 3.5 hours. Following the reaction the DNA was degraded by the addition of 5 µL of DNase and a 10 minute incubation at room temperature. Purification was performed via a Phenol/chloroform extraction. In strategy II, the tRNA expression gene cassette (including the Ipp promoter and rrnC terminator) was cloned at a PstI site within the pK7 vector (see attached sequence).

In this example we chose to incorporate o-methyl-L-tyrosine into pK7mGM-CSF_N75STOP. To perform this experiment it was also necessary to express and purify a tyrosine-synthetase mutant originating from *Methanococcus jannaschii*. The tyrosine-synthetase gene was cloned into the pK7 vector and a hexahistidine tag was attached to the C-terminus. The necessary synthetase mutations to enable o-methyl-tyrosine substitution were published by Wang et al., supra. BL21 DE3 cells were transformed with the synthetase mutant plasmid and were grown in LB media and induced at 0.6 OD with 1 mM IPTG. The cells were harvested at 3 OD and centrifuged at 7140×g for 30 minutes. The cells were then resuspended and washed in S30 buffer (10 mM Tris-Acetate pH8.2, 14 mM Mg Acetate, 60 mM K Acetate) three times in succession. The cell pellet was then resuspended and the cells were lysed via single pass homogenization (greater than 20,000 psi). The lysed cells were then centrifuged at 20,000×g for 30 min. The supernatant was then loaded onto a 1 mL Ni-NTA column (Amersham Biosciences), which was equilibrated with 10 mM imidazole, 50 mM phosphate buffer (pH 8.0), and 300 mM NaCl. The column was then washed with 30 mL of 25 mM imidazole in the same buffer and eluted with 250 mM imidazole in the same buffer. The purified products were then concentrated with Amicon Ultra-15 Centrifugal Filter Units (5,000 MWCO) and subsequently re-suspended and re-concentrated against phosphate buffered saline (PBS).

The standard PANOx-SP system that maintains an oxidizing environment which is (necessary for the formation and isomerization of disulfide bonds) was used in this example and contains the following components: 170 mM potassium glutamate, 10 mM ammonium glutamate, 16 mM magnesium glutamate, 33 mM phosphoenol pyruvate, 2.7 mM sodium oxalate, 0.6 mM ATP, 0.43 mM each of GTP, UTP, and CTP, 1.5 mM spermidine, 1.0 mM putrescine, 17 µg/mL folinic acid, 85.3 µg/mL $E.$ $coli$ tRNA mixture, 20 natural amino acids at 2 mM each, 10 µM L-[U-$^{14}$C]-Leucine, 0.33 mM nicotinamide adenine dinucleotide (NAD), 0.27 mM coenzyme A (CoA), 13.3 µg/mL pK7mGM-CSF_N75STOP, 0.1 mg/mL T7 RNA polymerase, 4 mM oxidized glutathione buffer (GSSG), 1 mM reduced glutathione buffer (GSH), 100 µg/mL of DsbC, and 0.24 volumes KC6 $E.$ $coli$ S30 extract pretreated for 30 minutes with 1 mM iodoacetamide (IAM). The extract was prepared as described by Zawada and Swartz Biotechnol Bioeng, 2006. 94(4): p. 618-24 and Liu et al, supra.

Figure 1:
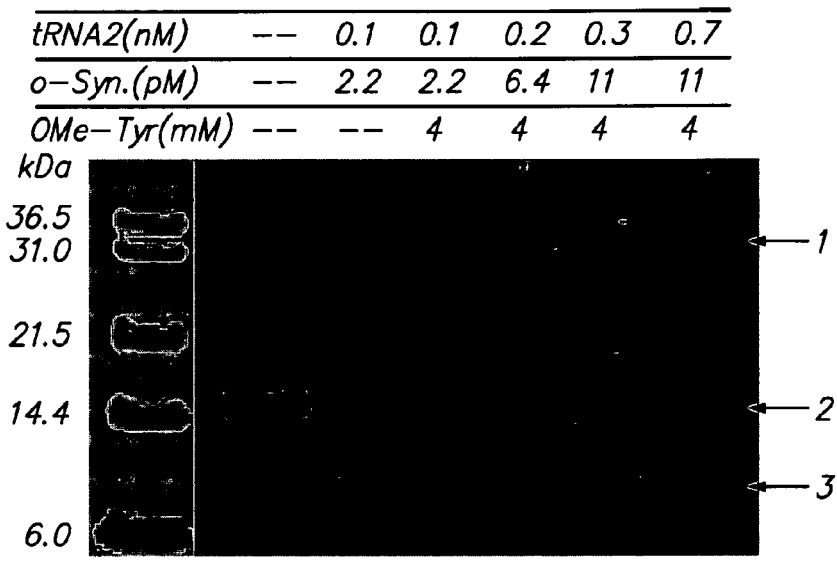
FIG. 1. Autoradiography analysis of o-methyl-tyrosine (OMe-Tyr) incorporation into mGM-CSF using unnatural amino acid incorporation strategy I. The amount of purified orthogonal (o-) *Methanococcus jannaschii* tRNA and o-methyl-tyrosine synthetase added was varied in the PANOx-SP cell-free reactions. The samples were run on a 10% Bis-Tris NuPAGE gel and compared to a Mark 12 molecular weight standard. Band 1 consists of dimeric protein products, Band 2 is full-length protein products which incorporated o-methyl-tyrosine and Band 3 is truncated protein product (truncated at residue 75). Lane 2 shows purified mGM-CSF standard with all natural amino acids.

Using the PANOx-SP system described above, after 3 hours of synthesis at 37° C., the synthesized protein was quantified by measuring TCA-precipitable radioactivity using a liquid scintillation counter (LS3801, Beckman Coulter, Inc.) and running an SDS-PAGE autoradiogram (10% Bis-Tris NuPAGE gel in MES buffer). Using strategy I, the maximum active, cell-free synthesized mGM-CSF following n=9 reactions (containing o-methyl-tyrosine) produced was approximately 50 ng/mL, as quantified from FIG. 1 and in agreement with scintillation counting results. As shown in FIG. 1, the amount of modified protein produced was at the lower limit of detection for these assays. Strategy II yielded similar low yields by producing 20±5 ng/mL in n=9 PANOx-SP cell free reactions.

Example 3

In Vivo Expression of Orthogonal tRNA and Synthetase

The standard PANOx-SP cell-free expression environment used in this example contains the following components: 170 mM potassium glutamate, 10 mM ammonium glutamate, 16 mM magnesium glutamate, 33 mM phosphoenol pyruvate, 2.7 mM sodium oxalate, 0.6 mM ATP, 0.43 mM each of GTP, UTP, and CTP, 1.5 mM spermidine, 1.0 mM putrescine, 17 µg/mL folinic acid, 85.3 µg/mL $E.$ $coli$ tRNA mixture, 20 natural amino acids at 2 mM each, 10 µM L-[U-$^{14}$C]-Leucine, 0.33 mM nicotinamide adenine dinucleotide (NAD), 0.27 mM coenzyme A (CoA), 13.3 µg/mL pK7CAT_Y109STOP, 0.1 mg/mL T7 RNA polymerase, and 0.24 volumes KC6 $E.$ $coli$ S30 extract containing in vivo expressed orthogonal rRNA and tRNA synthetase. Following transformation of the orthogonal tRNA and synthetase plasmid (pDule plasmid as published by Wang et al. supra.) into chemically competent KC6 cells, the extract was prepared as described by Zawada and Swartz, supra, and Liu at al, supra, (with modifications described below) and harvested at 3 OD.

Figure 2:
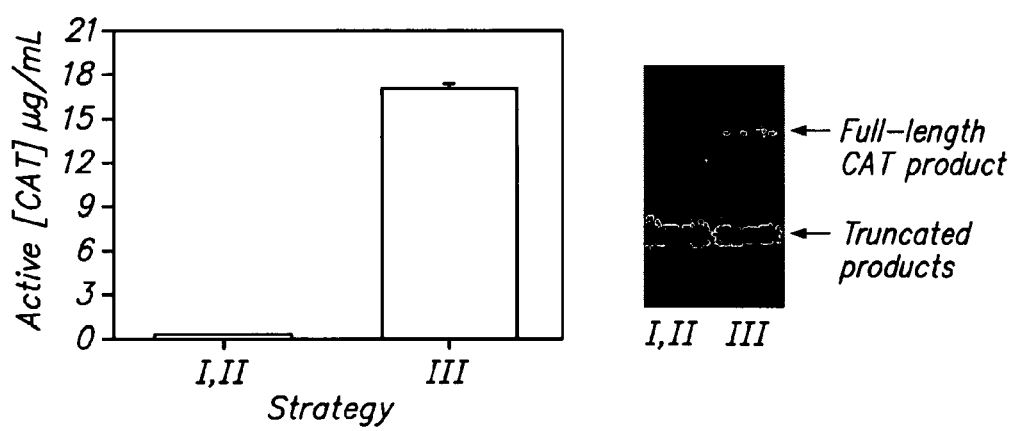
FIG. 2. Cell-free protein synthesis yields for the incorporation of o-methyl-tyrosine in chloramphenicol acetyl transferase (CAT) using different process development strategies. Active CAT concentrations were determined via a colorimetric based activity assay [26] and confirmed by scintillation counting after L-[U-$^{14}$C]-Leucine incorporation. Aoradiography analysis was conducted with a 10% Bis-Tris NuPAGE gel in MES buffer. This data is an average of n=6 experiments.

Strategy III involved the generation of cell extract from the modified cell strains expressing both orthogonal synthetase and orthogonal tRNA. Initially the procedure outlined by Zawada et al. Fermentation Biotechnology, ed. S. B. 2003, Washington, D.C.: ACS Press. 142-156 was followed to conduct the fermentation. However, the growth rates of $E.$ $coli$ A19 phenylalanine auxotroph strains and KC6 cell strains on defined media was approximately 0.5 to 0.6 hr$^{-1}$. This resulted in the production of cell extract that did not show significant improvements over strategies I and II (plotted in FIG. 2) at producing CAT modified protein within our cell-free system. Changing to 2×YTPG growth media increased the growth rate to 0.7 to 0.9 hr$^{-1}$ at 37° C. Following this improvement in growth rate, analytical characterization of the extracts was performed. It was found via analytical assays that the total protein concentration within the cell extract is acceptable (~42 mg/mL, determined by Bradford assay), the concentration of natural amino acids is low (<0.2 mM, quantified via a Dionex HPLC system) and vesicle concentration varies (0.5 to 3.5 mg/L, measured via a phosphate assay after chloroform extraction, (Chen et al. Anal. Chem., 1956. 28: p. 1756-1758 and Fiske and Subbarow, 1925, J. Biol. Chem., 66: p. 374-389. During system characterization it was found that increased vesicle concentrations aided in generating increased quantities of protein containing an unnatural amino acid. As shown in FIG. 2, CAT cell-free protein synthesis, which included 4 mM of o-methyl-tyrosine, yields increased to approximately 17 µg/mL of active CAT as a result of the system development. The autoradiogram shown in FIG. 2 (generated from a 10% Bis-Tris NuPAGE gel run in MES buffer) indicates an increased concentration of full-length protein product containing the unnatural amino acid and a decreased concentration of truncated protein product.

Example 4

In Vivo Expression of tRNA and the Addition of Purified Synthetase

Increasing the concentration of orthogonal synthetase and tRNA in the cell-free reaction increased cell-free product accumulation and decreased protein truncation at the amber stop codon. It was reasoned that the higher concentrations might overwhelm any proteases or nucleases that may be limiting orthogonal synthetase and tRNA concentrations and result in increased production of modified protein products.

In this approach, elevated orthogonal tRNA levels (using a modified pDULE vector where the tRNA synthetase gene was removed) were achieved and controlled during production of the cell extract (using defined media). However to minimize stress on the cell, the orthogonal synthetase was produced separately. For this experiment the $Methanococcus$ $jannaschii$ tyrosine-synthetase mutant that readily incorporated p-azido-phenylalanine was produced and purified. The necessary mutations were published by Chin at al., supra. This gene was inserted behind a T7 promoter, a hexahistidine tag was attached to the C-terminus, and the resultant plasmid was transformed into the BL21DE3 pLys cell strain. The cells were grown in LB media and induced at 0.6 OD with 1 mM IPTG. The culture was harvested at 3 OD and centrifuged at 7140×g for 30 minutes. The cells were then resuspended in S30 buffer (10 mM Tris-Acetate pH8.2, 14 mM Mg Acetate, 60 mM K Acetate) and centrifuged three times in succession. The cell pellet was then resuspended and the cells were lysed via single pass homogenization. The broken cells were then centrifuged at 20,000×g for 30 min. The supernatant was collected and incubated with DNase for 30 minutes at room temperature. The supernatant was then loaded on a 1 or 5 mL Ni-NTA column, which was equilibrated with 10 mM imidazole, 50 mM phosphate buffer (pH 8.0), and 300 mM NaCl. The column was then washed with 30 mL of 25 mM imidazole in the same buffer and eluted with 250 mM imidazole in the same buffer. The purified products were then concentrated with Amicon Ultra-15 Centrifugal Filter Units (5,000 MWCO) and dialyzed with 7,000 MWCO dialysis tubing against phosphate buffered saline (PBS).

Separately, the KC6 cell strain (the KGK10, MCJ29, ARG1, and ARG2 strains described previously could also have been used) containing the pK7tRNAmj plasmid was grown in a 4 or 10-liter fermentor on defined media. The fermentation was harvested at 3 OD and extract was prepared using an abbreviated procedure described by Liu at al. supra. This procedure was modified in the following ways: (1) No S30 buffer dilution was conducted following the homogenization centrifugations, and (2) A single dialysis step was performed. In some cases the final centrifugation following the 90 minute runoff reaction can be omitted to preserve a higher vesicle concentration. Procedures for determining vesicle concentration were obtained from Chen et al., supra, and Fiske and Subbarow, supra.

The unAA-PANOx-SP reaction conducted in this example included, 170 mM potassium glutamate, 10 mM ammonium glutamate, 0.6 mM ATP, 0.43 mM each of GTP, UTP, and CTP, 1.5 mM spermidine, 1.0 mM putrescine, 17 μg/mL folinic acid, 85.3 μg/mL E. coli tRNA mixture, 20 natural amino acids at 2 mM each, 4 mM of unnatural amino acid, 0 to 167 μg/mL of aminoacyl synthetase, 10 μM L-[U-$^{14}$C]-Leucine, 0.33 mM nicotinamide adenine dinucleotide (NAD), 0.27 mM coenzyme A (CoA), 13.3 μg/mL pK7CAT_Y109STOP, 0.1 mg/mL T7 RNA polymerase, and 0.24 volumes E. coli S30 extract. The sources of the cell extract are described above. The unAA-PANOx-SP system also includes 16 mM magnesium glutamate, 33 mM phosphoenol pyruvate, and 2.7 mM sodium oxalate. These reactions were run at 30° C. for the times noted.

Figure 3A:
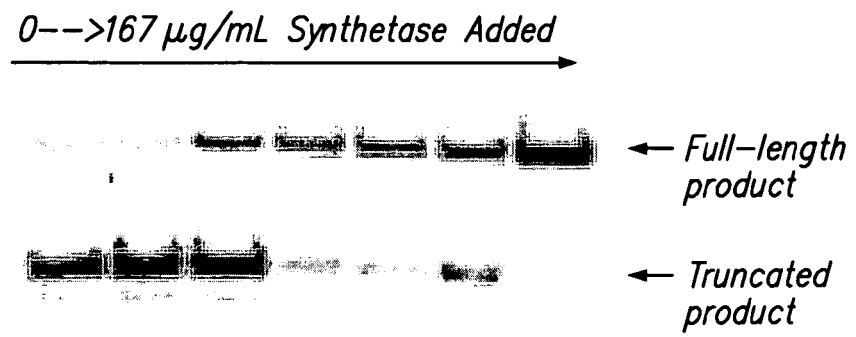
FIG. 3. Autoradiography analysis of CAT containing p-azido-phenylalanine (o-methyl-tyrosine and p-acetyl-phenylalanine results were similar). Autoradiograms were developed from 10% Bis-Tris NuPAGE gels run in MES buffer (A)
Figure 3B:
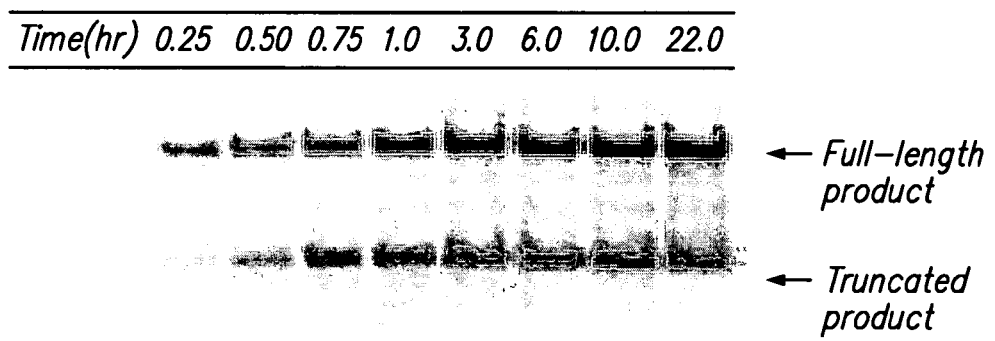
Figure 3C:
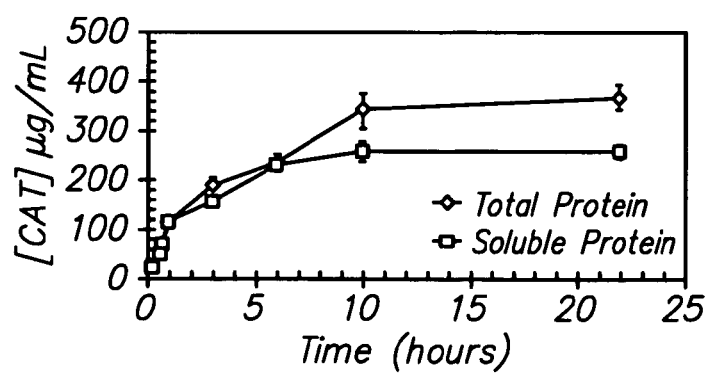

In strategy IV, the controlled expression of tRNA (from a modified pDule plasmid lacking the tRNA synthetase gene) during the extract preparation, the modified extract preparation protocol, and the addition of purified p-azido-phenylalanine synthetase to the unAA-PANOx-SP cell-free reaction resulted in increased modified protein yields. As seen in FIG. 3A, increasing the synthetase concentration increased the full-length active CAT yields approximately 10-fold above those shown in FIG. 2 (greater than 125 μg/mL). As determined via a colorimetric assay, 90 to 100% of the soluble CAT concentration is correctly folded, active protein. The changes in the extract preparation protocol aided in providing higher orthogonal tRNA and vesicle concentrations which are essential for prolonged modified protein synthesis for greater than 8 hours (see FIG. 3B). This ensures an active oxidative phosphorylation pathway, which is evident (see FIG. 3C) by the continued product formation following the initial consumption of PEP during the first hour of protein synthesis.

Example 5

Improving Cell Extracts for Unnatural Amino Acid Incorporation

Although active bacterial and mammalian secreted proteins were produced in our combined transcription/translation system, we sought higher yields. We found that one of the components that is limiting is the orthogonal synthetase concentration. One reason for this component being limited is shown in FIG. 4, lane 1. This is the orthogonal p-azido-phenylalanine tRNA synthetase protein product that was produced in the standard PANox-SP cell-free protein synthesis reaction at 37° C. for 3 hours. Reaction conditions were previously described in Example 2 (products were labeled with L-[U-$^{14}$C]-Leucine). The orthogonal synthetase appears to be subject to proteolytic degradation. This was further verified by adding greater than 500 μg/mL of L-[U-$^{14}$C]-Leucine labeled orthogonal synthetase into KC6 cell extract. Following a 6 hour incubation at 37° C., no full-length synthetase was detected via autoradiography. By controlling synthetase degradation we attempted to increase modified protein production.

Using cell strains that were previously generated in the Swartz lab (KGK10 and KC6) and have been shown to minimize disulfide reductase concentrations and stabilize amino acid concentrations, new cell strains were constructed. These cell strains were modified by deleting or mutating the ompT gene that encodes the outer membrane protein T such that the gene product would either be absent or would still be present in our cell-extract but would be inactive as a protease but active as a chaperone.

The MCJ29 mutant was generated as described by Jewett in his Ph.D. thesis, *Department of Chemical Engineering*. 2005, Stanford University: Stanford. p. 240. The ARG1 and ARG2 mutants were generated via gene replacement using pKO vectors [28] to construct plasmids for allelic exchange. Approximately 1 kb fragments flanking the gene ompT to be replaced were amplified from genomic DNA by PCR with primers ompTNo and ompTCo (based on sequences obtained from G.M. Church website). We cloned the PCR product from wild-type ompT into the pKOV vector using the suitable restriction enzymes NotI and SalI. We then introduced the desired D83A mutation into the wild-type ompT gene sequence using the QuikChange site-directed mutagenesis kit with primers ompTD83AmutF (SEQ ID NO:11) (GTG-GCAATATGGTCGCTCAGGACTGGATGG) and mutR (SEQ ID NO:12) (GGTAGGTCAAGGACTCGCTGG-TATAACGGTG). Mutant alleles cloned into the pKOV gene replacement vector were electroporated into KC6 (to eventually generate ARG1) or KGK10 (to eventually generate ARG2) and the cells were allowed to recover for 1 h at 30° C. The cells were plated on prewarmed chloramphenicol/LB plates and incubated at 42° C. To measure the integration frequency, the electroporated cells were also plated on chloramphenicol/LB plates at 30° C. From the 42° C. plate, 1 to 5 colonies were picked into 1 mL of LB broth, serially diluted, and immediately plated at 30° C. on 5% w/v sucrose plates. The colonies on the 5% sucrose plates were screened on chloramphenicol plates at 30° C. to test for loss of the replacement vector. To summarize, we looked for sucrose-resistant and chloramphenicol-sensitive colonies for the replacement event by "colony picking" and confirmed our choices by PCR with primers ompT5' and ompTD83A. What resulted were the new cell strains ARG1 and ARG2 which would contain the inactivating D83A mutation in the ompT gene.

As shown in FIG. 4. Autoradiography analysis of orthogonal synthetase accumulation after expression in a cell-free protein synthesis reaction. The autoradiogram was developed from a 10% Bis-Tris NuPAGE gel run in MES buffer. The p-azido-phenylalanine tRNA synthetase is severely degraded by proteases in the KC6 cell extract. The synthetase is not degraded when the ARG1, ARG2, or the MCJ29 mutant cell strains are used to produce the cell-extracts (a single example is given since all results were similar). When the ompT deletion or mutation is incorporated into KC6 or KGK10 cell strains, the newly produced synthetase is stable.

, lane 2, these genomic modifications to the cell strains used to make cell extracts nearly eliminated degradation of the p-azido-phenylalanine tRNAsynthetase when produced in a standard PANOx-SP reaction. The same result was observed when the p-acetyl-phenylalanine synthetase was incubated with ARG1 and MCJ29 extracts at 37° C. for 6 hours.

Example 6

High Level Production of Bacterial Proteins Containing Unnatural Amino Acids in a Cell-Free Platform While any of the alternative energy systems listed previously could have been used, the unAA-PANOx-SP was chosen to exemplify increased production of protein containing an unnatural amino acid. Specifically, for this example the cell-free reaction included, 170 mM potassium glutamate, 10 mM ammonium glutamate, 0.6 mM ATP, 0.43 mM each of GTP, UTP, and CTP, 1.5 mM spermidine, 1.0 mM putrescine, 17 µg/mL folinic acid, 85.3 µg/mL E. coli tRNA mixture, 20 natural amino acids at 2 mM each, 2 mM of unnatural amino acid, 150 µg/mL of aminoacyl tRNA synthetase, 10 µM L-[U-$^{14}$C]-Leucine, 0.33 mM nicotinamide adenine dinucleotide (NAD), 0.27 mM coenzyme A (CoA), 13.3 µg/mL template plasmid, 0.1 mg/mL T7 RNA polymerase, and 0.29 volumes of S30 extract (prepared using one of the specified cell lines) containing the orthogonal *Methanococcus jannaschii* tRNA. The sources of the cell extract are described above. The unAA-PANOx-SP system also includes 16 mM magnesium glutamate, 33 mM phosphoenol pyruvate, and 2.7 mM oxalic acid.

FIG. 5 shows the significant increases (compared to data shown in FIG. 2) in the production of CAT that contains p-azido or p-acetyl-phenylalanine. Strategies I and II display similar yields to those shown in FIG. 1 for mGM-CSF. Similarly, strategy IIIa verifies the improved modified protein production shown in Example 3, FIG. 2. Additionally, strategy IIIb verifies the reproducibility and synthetase limitation shown in FIG. 3. Lastly, using the composition listed in this example, strategy IIIc shows that optimization of unAA-PANOx-SP component ratios (unnatural amino acid, orthogonal synthetase, and cell extract), optimization of the reaction environment (30° C. for 8 hours), the use of mutated cell strains for extract preparation (ARG1 and ARG2), and modification of the procedure by which they are produced, and incorporation of the pK7tRNAmj plasmid into the new cell-strains, a new bacterial-based cell-free system produced 2 to 3-fold additional modified protein (greater than 300 µg/mL) containing p-azido or p-acetyl-phenylalanine. These yields were approximately 75% of the wild-type CAT protein produced in a similar cell-free reaction (without the addition of unnatural amino acids). Additionally, as seen in FIG. 5, analysis of strategy 111c protein products via autoradiography showed that the cell-free reaction product is primarily full-length protein containing an unnatural amino acid.

Example 7

Synthesis of Bioactive Mammalian Secreted Proteins Containing an Unnatural Amino Acid Given the design of a new bacterial-based cell-free system and increased CAT yields it was appropriate to begin incorporating unnatural amino acids into a number of different complex proteins that had not been produced with an unnatural amino acid. The examples of complex proteins shown in this report are mGM-CSF, hGM-CSF, and the TetA membrane protein. Such a platform technology can be extended to a large number of complex proteins that are not shown as examples, including but not limited to fusion proteins, single chain variable fragments (scFvs), Fab antibody fragments, and full length antibodies.

Following unAA-PANOx-SP cell-free reactions similar to those described in Example 6, the active protein yields from pK7mGM-CSF_N75STOP, pK7hGM-CSF_N36STOP, or pK7hGM-CSFOPT_N36STOP were determined via cell proliferation based assays. To ensure correct folding, the unAA-PANOx-SP system described by Example 6 was modified to maintain an oxidizing protein folding environment by supplementing the reaction mix with 4 mM GSSG, 1 mM GSH, and approximately 100 µg/mL DsbC. Additionally, cell extracts were pretreated with 1 mM iodoacetamide (IAM). A small volume of concentrated IAM was first added to the reaction vessel. A much larger volume of S30 extract was then rapidly and thoroughly mixed with the small volume of IAM. The extract was incubated with the IAM for 30 minutes at room temperature before being used in the cell-free reaction. The KC6 cell strain containing the modified pDule plasmid (lacking the tRNA synthetase gene) was used to make the cell extract and the cell-free reactions were conducted at 30° C. for 6 hours.

The biological activity of the murine and human GM-CSF was assayed using an mGM-CSF or hGM-CSF-dependent cell line, NFS-60 or TF1 (purchased from ATCC). The soluble cell-free expressed proteins and the murine and human GM-CSF commercial standards were serially diluted in triplicate. Equal volumes of RPMI media with 10% FCS and the log phase cell culture were added to the serially diluted cell-free products and the GM-CSF standards to test their ability to stimulate cell proliferation. Cells were plated at a concentration of 5000 cells in flat-bottom 96-well tissue culture plates. After incubation at 37° C. and 5% $CO_2$ for 16-20 hours for NSF-60 cells and 36 to 48 hours for TF1 cells, 50 µL of [$^3$H]-Thymidine was added to each well at a final concentration of 6.7 µCi/mL, and proliferation was monitored by the incorporation of [$^3$H]-Thymidine. Following 8-10 hours of incubation at 37° C. and 5% $CO_2$, the cells were harvested onto glass fiber filter mats and washed. The [$^3$H]-Thymidine incorporation was measured using a Wallach 1450 Microbeta scintillation counter (Perkin Elmer Life Sciences).

The unAA-PANOx-SP cell-free protein synthesis yields for modified, disulfide bonded proteins are shown in FIG. 6. Additionally, the proteins produced are correctly folded and biologically active as shown in the bioactivity data (method described previously) plotted in FIG. 7. These results show that the new cell-free system produces active, disulfide bonded proteins that contain an unnatural amino acid with GM-CSF activity comparable to that produced by an in vivo system. Those cell-free reactions containing either no orthogonal tRNA, no synthetase, or no unnatural amino acid did not generate any protein that stimulated cell proliferation. These data also suggest that fusion protein constructs with GM-CSF or a similar immune stimulant at the N or C-terminus could have an unnatural amino acid incorporated into them and be produced via this new cell-free protein synthesis platform.

Example 8

Incorporation of an Unnatural Amino Acid into a Membrane Protein

Use of the glutamate phosphate cell-free system to produce correctly folded membrane proteins is unique in that it also requires the preparation of a vesicle solution by using a method adapted from Muller and Blobel Proc Natl Acad Sci USA, 1984. 81(24): p. 7737-41 and Osborn et al J Biol Chem, 1972. 247(12): p. 3962-72. KC6 cells were resuspended and washed in 20 mM Tris-HCl pH 8.0, 1 mM EDTA. The final cell pellet was resuspended in 1 mL of the same buffer per gram of cells and incubated on ice with 0.2 mg/mL of hen egg white lysozyme for 15 min. After incubation, the cell solution was passed through a homogenizer three times at 20,000 psi. Unbroken cells and debris were removed by two centrifugations at 30,000×g for 20 min each. Then the vesicles were collected by ultracentrifugation (154,000×g, 1.5 hr), and pelleted again through 0.5 mL/g cells of a solution containing 250 mM sucrose in buffer H (20 mM HEPES-KOH pH 7.5, 1 mM DTT, 5 mM EDTA) at 231,000×g for 1 hr. These crudely purified vesicles are resuspended in 20% (w/w) sucrose and loaded on top of a step gradient containing layers of 50%, 45%, 40%, 35%, 30%, and 25% (w/w) sucrose. After ultracentrifugation for 24 hrs at 114000×g, the fractions containing inner membrane vesicles are collected. These vesicles are pelleted and finally resuspended to high concentration (1-2 mg/mL) in 20 mM HEPES-KOH pH 7.2, 60 mM KCl, 1 mM DTT.

Having generated the cell-free components, we used the combined glutamate phosphate transcription/translation system to synthesize the membrane protein, TetA, containing an unnatural amino acid (p-azido-phenylalanine) and assess if it could be properly folded into vesicle membranes. The components of the glutamate phosphate cell-free reaction used to incorporate an unnatural amino acid include 13.3 µg/mL pK7TetA_D34STOP or pK7TetA_Q182STOP (see attached sequences), 1.2 mM AMP, 0.86 mM CMP, 0.86 mM GMP, 0.86 mM UMP, 34 µg/mL folinic acid, 170.6 µg/mL *E. coli* tRNA mixture, 2 mM each of 20 natural amino acids, 4 mM of the unnatural amino acid, 75 µg/mL of aminoacyl synthetase, 0.33 mM nicotinamide adenine dinucleotide (NAD), 0.27 mM coenzyme A (CoA), 1 mM putrescine, 1.5 mM spermidine, 4 mM sodium oxalate, 1 mM dithiothreitol, 10 mM ammonium glutamate, 130 mM potassium glutamate, 8 mM magnesium glutamate, 10 mM potassium phosphate pH 7.2, 12 µM [14C]-Leucine, 0.1 mg/mL T7 RNA polymerase, 0.29 volumes of *E. coli* S30 extract, and 0.21 volumes of inner membrane vesicle solution.

Figure 8A:
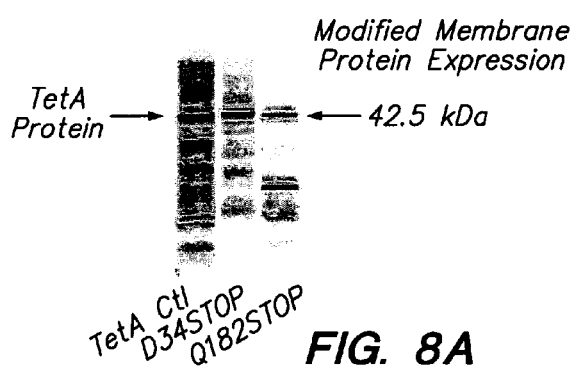

It is clear from the FIG. 8A autoradiogram that we can produce the TetA membrane protein (42.5 kDa) that contains the unnatural amino acid. This was after 6 hrs of cell-free protein synthesis at 37° C. The total synthesized protein was quantified by measuring TCA-precipitable radioactivity using a liquid scintillation counter. This was calculated to be 226 and 349 µg/mL for the TetA mutant proteins generated from plasmids pK7TetA_D34STOP and pK7TetAQ182STOP. Before further analysis, the reaction was crudely purified by dialysis in a 100 kDa MWCO dialysis bag against 500-1000 volumes of 10 mM Tris-HCl pH 8.0, 100 mM KCl, with buffer exchange three times after dialysis for at least 3 hours each time.

Figure 8B:
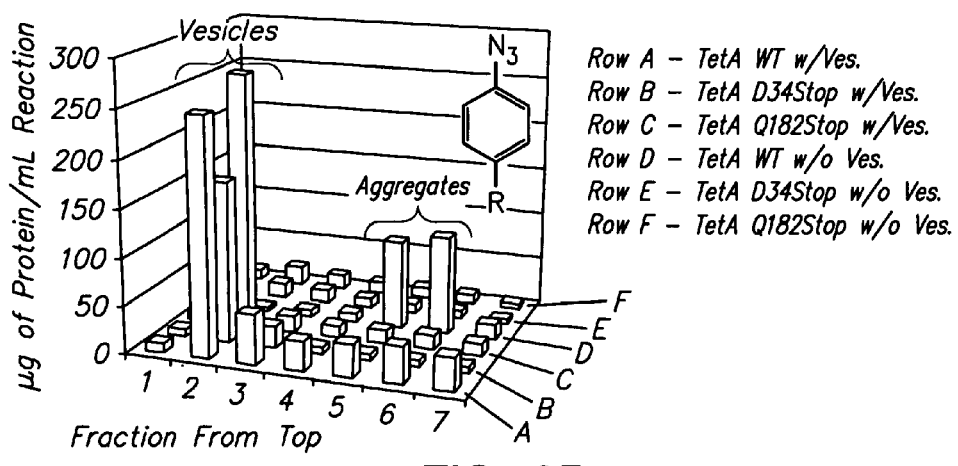

To quantify the amount of protein inserted into the *E. coli* vesicles, we subjected the dialyzed cell-free reaction products to a sucrose flotation assay. The dialyzed cell-free reaction product is mixed with a dense sucrose solution and loaded at the bottom of a three step sucrose gradient. The densities of the layers are chosen such that, after ultracentrifugation (16 hrs, 237,000×g), the misfolded protein aggregates (with density ρ~1.3 g/mL) stay in the bottom layer while the lighter vesicles (ρ~1.13-1.25 g/mL, depending on how much protein has been inserted) float to the interface above the second layer. FIG. 8 shows the distribution of radiolabeled TetA after sucrose floatation analysis. 6M urea has been added throughout the gradients to reduce non-specific association of the synthesized protein with membranes. When vesicles are present in the reaction, we see that a majority of the synthesized TetA is associated with the vesicles (fraction 2). This association does not occur when the vesicles are not added to the protein synthesis reaction, as indicated by the retention of aggregated TetA in the lower fractions (fractions 6-8). The reactions containing no additional vesicles did not show a large amount of membrane associated or aggregated protein product. This highlights the importance of oxidative phosphorylation in the production of proteins containing unnatural amino acids. Such a pathway is not as active when additional vesicles are not present. As seen in FIG. 8B, the amount of TetA shown to be inserted into vesicles corresponds to an overall yield of greater than 100 µg of inserted TetA per mL of cell-free reaction. Apparently the truncated 182 amino acid TetA is also inserted since the majority of product from the Q182STOP reaction was both truncated and vesicle associated (see FIG. 8A).

To ensure that our membrane protein was inserted appropriately into the vesicles we exposed the dialyzed reaction mixture to 0.2 µg/µL of the non-specific protease Proteinase K. Portions of the membrane protein that are not embedded in the membrane—such as cytoplasmic domains or large loops between transmembrane segments—are degraded more quickly by the protease as compared with segments within the membrane or in the vesicle interior. Thus, by observing the protein fragments generated by Proteinase K digestion over time, we could verify whether the protein had the expected topology that corresponds with proper folding.

FIG. 9 shows the band profile obtained after incubation with Proteinase K at 25° C. Even after 60 min, a significant fraction of full-length TetA is still present in the vesicles. However, if the membranes are dissolved with LDS detergent, the TetA is no longer protected from digestion. Thus, the TetA is incorporated into the vesicle membranes.

These data demonstrate the synthesis of high yields of modified membrane proteins using a cell-free expression system; and further show that the synthesized protein is inserted into vesicles and properly folded.

Example 9

Synthesis of Optimized MS2 Gene

Materials and Methods

Plasmid Construction The MS2 Coat Protein gene was optimized for both *E. coli* tRNA relative concentrations (preferred codons) and synthesis from oligonucleotides using DNAworks. Oligonucleotides (60 bp average length, Operon Technologies, USA) based on sequences recommended by DNAworks were assembled into the optimized MS2 coat protein gene nucleotide sequence using two-step PCR. pET24a-MS2 cp was generated by ligation (T4 DNA ligase, NEB, USA) of the optimized MS2 coat protein sequence into the pET-24a(+) vector (Novagen, USA) at the Nde I and Sal I restriction sites. pET24a-MS2 cp was transformed into DH5a cells (One Shot MAXX Efficiency DH5α-T1$^R$ Competent Cells, Invitrogen) and the plasmid was purified with Qiagen Plasmid Maxi Kit (Qiagen, Valencia, Calif.). Using two-step PCR and custom oligonucleotides (Operon Technologies, USA), a T15STOP (amber stop codon) substitution was mutated into the MS2 cp sequence. The mutated sequence was ligated into the pET24a(+) vector (Novagen, USA) at the Nde I and Sal I restriction sites and named pET24a_MS2 cp_T15STOP. The vector was transformed into DH5a cells (One Shot MAXX Efficiency DH5α-T1$^R$ Competent Cells, Invitrogen) and the plasmid was purified with Qiagen Plasmid Maxi Kit (Qiagen, Valencia, Calif.) for use in cell-free protein synthesis reactions. The optimized coat protein sequence is provided as SEQ ID NO:9.

Example 10

Expression of MS2 Coat Protein containing an Unnatural Amino Acid

Materials and Methods

PANOx-SP Cell-free Expression System. The PANOx-SP cell-free reactions[6] conducted in this example were 30 µL in volume and were incubated at 30° C. for 8 hr in 1.5 ml eppendorf tubes. The reaction includes the following components: 1.2 mM ATP, 0.85 mM each of GTP, UTP, and CTP, 34 µg/mL folinic acid, 170.6 µg/mL E. coli tRNA mixture, 24 nM pET24aMS2_T15STOP plasmid, 100 µg/mL T7 RNA polymerase, 5 µM I-[KU-$^{14}$C]-Leucine, 2 mM each of 20 unlabeled amino acids, 4 mM p-azido-phenylalanine, ~150 µg/mL of pure Methanococcus jannaschii mutated tyrosine-synthetase, 0.33 mM nicotinamide adenine dinucleotide (NAD), 0.27 mM coenzyme A (CoA), 30 mM phosphoenolpyruvate, 1.5 mM spermidine, 1 mM putrescine, 170 mM potassium glutamate, 10 mM ammonium glutamate, 20 mM magnesium glutamate, 2.7 mM sodium oxalate, and 28% v/v of KC6_tRNA S30 extract, prepared as described below. T7 RNA polymerase is prepared from E. coli strain BL21 (pAR1219) as described by Grodberg and Dunn.

Purification of the Methanococcus jannaschii Orthogonal Tyrosine Synthetase.

For this experiment the Methanococcus jannaschii tyrosine-synthetase mutant that readily incorporated p-azido-phenylalanine was produced and purified. The necessary mutations were published by Chin et al., supra. This gene was inserted behind a T7 promoter, a hexahistidine tag was attached to the C-terminus, and the resultant plasmid was transformed into the BL21DE3 pLys cell strain. The cells were grown in LB media and induced at 0.6 OD with 1 mM IPTG. The cells were harvested at 3 OD and centrifuged at 7140×g for 30 minutes. The cells were then resuspended and washed in S30 buffer (10 mM Tris-Acetate pH 8.2, 14 mM Mg Acetate, 60 mM K Acetate) three times in succession. The cell pellet was then resuspended and the cells were lysed via single pass homogenization. The broken cells were then centrifuged at 20,000×g for 30 min. The supernatant was collected and incubated with DNase for 30 minutes at room temperature. The supernatant was then loaded on a 1 or 5 mL Ni-NTA column, which was equilibrated with 10 mM imidazole, 50 mM phosphate buffer (pH 8.0), and 300 mM NaCl. The column was then washed with 30 mL of 25 mM imidazole in the same buffer and eluted with 250 mM imidazole in the same buffer. The purified products were then concentrated with Amicon Ultra-15 Centrifugal Filter Units (5,000 MWCO) and dialyzed with 7,000 MWCO dialysis tubing against phosphate buffered saline (PBS).

Production of S30 Extract Containing High Concentrations of Orthogonal tRNA. In this approach, elevated orthogonal tRNA levels (using the tRNAmj gene, SEQ ID NO:10, inserted into the pK7 vector) were achieved and controlled during production of the cell extract. Extracts were generated with the pK7tRNAmj plasmid expressed during growth of cell strain KC6 (A19ΔtonAΔtnaAΔspeAΔendAΔsdaAΔsdaBΔgshA met$^+$). The KC6 cell strain (KGK10, MCJ29, ARG1, and ARG2 could also have been used) containing the pK7tRNAmj plasmid (referred to as KC6_tRNA) was grown in a 4-liter fermentor on defined media. (18) The fermentation was harvested at 3 OD and extract was prepared using an abbreviated procedure of Liu et al. This procedure was modified in the following ways: (1) No S30 buffer dilution was conducted following the homogenization centrifugations, (2) A single dialysis step was performed.

Protein Yield Determination Total synthesized protein yields were determined by TCA-precipitation and radioactivity measurements in a liquid scintillation counter (LS3801, Beckman Coulter, Inc.). Soluble yields were determined by TCA-precipitation and scintillation counting of the supernatants following sample centrifugation at 25° C. and 15,000 RCF for 15 min.

Results

30 µL PANOx SP system cell-free reactions using pET24a_MS2 cp_T15STOP were performed and the total and soluble yields were determined to be 77 µg/ml (±6.6 µg/ml) and 63 µg/ml (±3.2 µg/ml) respectively as indicated in FIG. 10.

Example 11

Demonstrating Assembly of MS2 VLP with p-azido-phenylalanine incorporation

Materials and Methods:

SDS-PAGE and Autoradiography Soluble proteins were separated from insoluble fractions by centrifugation at 15,000×g for 15 min. Sample was applied to a NuPAGE 10% Bis-Tris Gel (Invitrogen, La Jolla, Calif.) run in MES buffer with Mark12 MW Standard (Invitrogen) molecular weight markers. Gels were stained with Commassie Blue Stain (Bio-Rad) and dried with a gel dryer, model 583 (Bio-Rad, Richmond, Calif.) before being exposed to Kodak scientific imaging films (Rochester, N.Y.).

Dialysis To remove unincorporated L-[U-$^{14}$C]-Leucine, the cell-free produced was dialyzed in 6-8000 MWCO Specra/Pro Molecularporous Membrane Tubing (Spectrum Labs) against 300 mL TSM buffer (10 mM Tris-HCl, 100 mM sodium chloride, 1 mM magnesium chloride, pH 7.0) overnight with 2 buffer exchanges.

Sucrose Step-Gradient Velocity Sedimentation The dialyzed cell-free rxn product was subjected to sucrose discontinuous gradient centrifugation. Polyallose 16×102 mm Centrifuge Tubes (Beckman, Palo Alto, Calif.) were successively filled with 1 mL of sucrose solution decreasing by 2.5% w/v (40%, 37.5%, 35%, 32.5%, 30%, 27.5%, 25%, 22.5%, 20%, 17.5%, 15%, 12.5%, 10% w/v) in TSM buffer and 15 mM EDTA. The dialyzed cell-free reaction product was layered on top of the tube and centrifugation was performed at 31,000 rpm in a Beckman-Coulter SW-32 swinging bucket rotor (Fullerton, Calif.) in a Beckman L8-M ultracentrifuge at 4° C. for 3.5 hr with "slow" acceleration (profile 9) and "no brake" deceleration. The 0.5 mL fractions were collected using a Teledyne Isco Foxy Jr. Density Gradient Fractionation System (Lincoln, Nebr.) and the MS2 coat protein concentration in each fraction was determined by TCA-precipitation and radioactivity measurement using a liquid scintillation counter (LS3801, Beckman Coulter, Inc.).

Sucrose Gradient Fraction Radiolabeled MS2 Coat Protein Yield Determination MS2 coat protein yields in each sucrose gradient fraction were determined by radioactivity measurements after 50 μL of each fraction was spotted on individual chromatography papers (Whatman, USA) and allowed to dry. The chromatography papers were immersed in 5 mL of Beckman Readysafe Scintillation Cocktail and radiation was counted in a liquid scintillation counter (LS3801, Beckman Coulter, Inc.). The radiation count was converted to a yield based on the molecular weight of the MS2 coat protein and the number of leucines in MS2 coat protein where radiolabeled leucine could be incorporated.

VLP Concentration Sucrose gradient factions containing VLPs were concentrated by filling Amicon Ultra-4 100,000 MWCO Centrifugal Filter Devices with gradient fractions and TSM buffer to 4 mL. The units were centrifuged for 15 min at 5,500 rpm and 4° C. in a Sorvall RCSB Centrifuge with a Fiberlite F13-14x15cy rotor (Piramoon Tech.) and Fiberlight 15 mL adaptors (Piramoon). The concentrated sample was immediately removed and stored at 4° C.

Results

To verify that all protein produced in the PANOx-SP modified cell-free reaction with the pET24a_MS2 cp_T15STOP vector included the p-azido-phenylalanine unnatural amino acid, a positive and negative control were run in parallel. The negative control was performed under the same conditions except in the absence of the orthogonal synthetase. The positive control reaction was run with the pET24a_MS2 cp vector in the PANOx-SP modified cell-free reaction. The assembly yield of p-azido-phenylalanine incorporated MS2 coat protein expressed by the pET24a_MS2 cp_T15STOP vector in the prokaryote based cell-free reaction described in the methods section and determined by sucrose gradient velocity sedimentation followed by radiation counting was 22 μg/mL (+/− 0.6 μg/mL, n=2) which is as indicated in FIG. 11.

Example 12

Validating Assembly of MS2 VLP with 180 Accessible p-azido-phenylalanines via a ThermoFinnigan LCQ Deca XP+ ion trap LC-MS Materials and Methods Mass Spectrometry Protocol Concentrated unnatural amino acid incorporated MS2 capsid and a control wild-type MS2 capsid sample were concentrated using Amicon-ultra 4 membrane filters. These samples were obtained from assembled MS2 VLP collected from sucrose density gradient samples similar to those shown in FIG. 11. The samples were applied to a SDS-PAGE NuPAGE 10% Bis-Tris Gel (Invitrogen, La Jolla, Calif.). The gel was run with MES running buffer (Invitrogen) for 60 min at 60 mA with Mark12 MW Standard (Invitrogen) molecular weight marker and stained with SimplySafe Stain (Invitrogen). The gel was destained by soaking in water overnight with a minimum of water rinses. Bands at 13.7 kD were cut from the wet gel excluding as much of the surrounding blank gel as possible.

To the gel cutout fragments, 10 mL of 45 mM dithiothreitol (DTT, Sigma) and 100 mL of 100 mM Tris pH 7.8 were added, and the sample was incubated at 55° C. for 30 minutes, following which the solution phase was discarded. Next 10 mL of 100 mM acrylamide (ICN) and 100 mL of 100 mM Tris pH 7.8 was added to the gel fragments and the mixture was incubated at room temperature for 30 minutes. Once again the solution phase was discarded. The gel pieces were then washed with 500 mL of 50 mM Tris pH 7.8/50% acetonitrile (ICN) for 30 minutes and the solution phase was discarded. The gel fragments were subsequently dried to completion in a SpeedVac rotary evaporation device. Finally, 5 pmol of chymotrypsin in 25 mM Tris pH 7.8 was added to gel fragments and upon swelling, sufficient 25 mM Tris pH 7.8 was added to allow the solution to just to cover the gel fragments. The fragments were incubated overnight at 37° C. The solution phase was removed and injected without further treatment into a ThermoFinnigan LCQ Deca XP+ ion trap LC-MS and analyzed.

Results

FIG. 13A shows the HPLC trace of the chymotrypsin digested fragment of the MS2 wild type capsid monomer that includes the T15 amino acid (881.6 m/z). Following digestion, the sequence of the fragment containing T15 was (SEQ ID NO:13) VLVDNGGTGDVTVAPSNF, MW=1761.91, m/z=882. FIG. 13B shows the MS2 wild-type monomer sample and shows the region of the HPLC trace where we would expect the same fragment as shown in FIG. 13A to appear if it contained the unnatural amino acid (912 m/z). The sequence of the fragment containing the T15p-azido-phenylalanine is expected to be (SEQ ID NO:13) VLVDNGGXGDVTVAPSNF, and its expected molecular weight and mass to charge ratio are expected to be MW=1821, m/z=912. As expected the wild-type MS2 control sample does not contain the unnatural amino acid since a peak is not seen following the chymotrypsin digest that would correspond with where we expect the unnatural amino acid incorporated fragment to elute.

FIG. 13C shows a chromatogram of the MS2 capsid substituted at the T15 position with p-azido-phenylalanine. As noted previously, this is the region we would expect our fragment to be if the unAA were not incorporated. Clearly, this is not the case. Lastly, FIG. 13D shows the HPLC trace and measured charge to mass ratio for the MS2 monomer sample containing the T15p-azido-phenylalanine substitution. The peak elutes where expected and has the expected mass to charge ratio for the peptide fragment with the unnatural amino acid incorporated. These results allow us to conclude that we have successfully incorporated p-azido-phenylalanine on an external epitope of the MS2 viral capsid.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for synthesis of at least one polypeptide containing at least one site specific unnatural amino acid in a cell-free in vitro reaction, the method comprising:
synthesizing the polypeptide in a cell-free in vitro translation reaction mix comprising an orthogonal tRNA that base pairs with a nonsense codon, a bacterial cell extract in which ompT is inactive, components of polypeptide and/or mRNA synthesis machinery; a template for transcription of the polypeptide; monomers for synthesis of the polypeptide; and co-factors, enzymes and other reagents necessary for translation; wherein the reaction mix comprises exogenously synthesized orthogonal tRNA synthetase that aminoacylates the orthogonal tRNA with an unnatural amino acid added to the reaction mix at a concentration of at least 30 µg/ml;
wherein the polypeptide is synthesized with at least one site specific unnatural amino acid, wherein said reaction mixture produces at least about 50 µg/ml of protein containing at least one site specific unnatural amino acid at a pre-determined site, wherein at least 50% of said protein containing at least one site specific unnatural amino acid is biologically active.

2. The method of claim 1, wherein said protein containing at least one site specific unnatural amino acid is synthesized in a coupled transcription translation reaction.

3. The method according to claim 1, wherein the orthogonal tRNA base pairs with a stop codon.

4. The method according to claim 1, wherein oxidative phosphorylation is activated in the cell-free in vitro translation reaction.

5. The method according to claim 4, wherein exogenous membrane vesicles are added to said cell-free in vitro translation reaction.

6. The method according to claim 1, wherein said protein containing at least one site specific unnatural amino acid is a membrane-bound protein.

7. The method according to claim 1, wherein said protein containing at least one site specific unnatural amino acid is a secreted protein.

8. The method according to claim 1, wherein said protein containing at least one site specific unnatural amino acid comprises at least one disulfide bond.

9. The method according to claim 1, wherein the polypeptide is a virus coat protein.

10. The method according to claim 9, wherein two or more species of coat protein are synthesized.

11. The method according to claim 9, wherein the virus coat protein is a bacteriophage coat protein.

12. The method according to claim 11, wherein said bacteriophage is MS2.

13. The method of claim 1, wherein the unnatural amino acid provides a reactant group not normally present in the amino acid.

14. The method of claim 13, wherein the unnatural amino acid is a modified phenylalanine or tyrosine.

15. The method of claim 1, wherein the unnatural amino acid is modified at the ortho or para position.

16. The method of claim 15, wherein the unnatural amino acid is chosen from p-acetyl-phenylalanine, p-ethynyl-phenylalanine, p-propargyloxyphenylalanine, and p-azido-phenylalanine.

* * * * *

SEQUENCE LISTING

<160> NUMBER OF SEQ ID NOS: 13

<210> SEQ ID NO 1
<211> LENGTH: 3371
<212> TYPE: DNA
<213> ORGANISM: E. coli

<400> SEQUENCE: 1

```
tcgacggatc gttccactga gcgtcagacc ccgtagaaaa gatcaaagga tcttcttgag      60
atccttttt tctgcgcgta atctgctgct tgcaaacaaa aaaaccaccg ctaccagcgg      120
tggtttgttt gccggatcaa gagctaccaa ctcttttcc gaaggtaact ggcttcagca      180
gagcgcagat accaaatact gtccttctag tgtagccgta gttaggccac cacttcaaga      240
actctgtagc accgcctaca tacctcgctc tgctaatcct gttaccagtg gctgctgcca      300
gtggcgataa gtcgtgtctt accgggttgg actcaagacg atagttaccg gataaggcgc      360
agcggtcggg ctgaacgggg ggttcgtgca cacagcccag cttggagcga acgacctaca      420
ccgaactgag atacctacag cgtgagcatt gagaaagcgc cacgcttccc gaagggagaa      480
aggcggacag gtatccggta agcggcaggg tcggaacagg agagcgcacg agggagcttc      540
caggggggaaa cgcctggtat ctttatagtc ctgtcgggtt cgccaccctc tgacttgagc      600
gtcgattttt gtgatgctcg tcaggggggc ggagcctatg gaaaaacgcc agcaacgcgg      660
ccttttttacg gttcctggcc tttgctggc cttttgctca catgttcttt cctgcgttat      720
cccctgattc tgtggataac cgtattaccg cctttgagtg agctgatacc gctcgccgca      780
gccgaacgac cgagcgcagc gagtcagtga gcgaggaagc ggaagaagct cgcacgccaa      840
tacgcaaacc gcctctcccc gcgcgttggc cgattcatta atgcagctgg cacgacaggt      900
ttcccgactg gaaagcgggc agtgagcgca acgcaattaa tgtgagttag ctcactcatt      960
aggcacccca ggctttacac tttatgcttc cggctcgtat gttgtgtgga attgtgagcg     1020
gataacaatt tcacacagga aacagctatg accatgatta cgaattcaga tctcgatccc     1080
gcgaaattaa tacgactcac tatagggaga ccacaacggt ttccctctag aaataatttt     1140
gtttaacttt aagaaggaga tatacatatg gagaaaaaa tcactggata taccaccgtt     1200
gatatatccc aatggcatcg taaagaacat tttgaggcat ttcagtcagt tgctcaatgt     1260
acctataacc agaccgttca gctggatatt acggcctttt taaagaccgt aaagaaaaat     1320
aagcacaagt tttatccggc ctttattcac attcttgccc gcctgatgaa tgctcatccg     1380
gaattccgta tggcaatgaa agacggtgag ctggtgatat gggatagtgt tcaccttgt     1440
tacaccgttt tccatgagca aactgaaacg ttttcatcgc tctggagtga ataccacgac     1500
gatttccggc agtttctaca catatattcg caagatgtgg cgtgttacgg tgaaaacctg     1560
gcctatttcc ctaaagggtt tattgagaat atgttttcg tctcagccaa tccctgggtg     1620
agtttcacca gttttgattt aaacgtggcc aatatggcaa cttcttcgcc cccgttttca     1680
ccatgggcaa atattatacg caaggcgaca aggtgctgat gccgctggcg attcaggttc     1740
atcatgccgt ttgtgatggc ttccatgtcg gcagaatgct taatgaatta caacagtact     1800
gcgatgagtg gcagggcggg gcgtaagtcg accggctgct aacaaagccc gaaaggaagc     1860
tgagttggct gctgccaccg ctgagcaata actagcataa ccccttgggg cctctaaacg     1920
ggtcttgagg ggttttttgc tgaaaggagg aactatatcc ggataacctc gagctgcagg     1980
gcatgcaagc ttggcactgg ccgtcgtttt acaacgtcgt gactgggaaa accctggcgt     2040
```

```
tacccaactt aatcgccttg cagcacatcc cccttt cgcc agctggcgta atagcgaaga      2100
ggcccgcacc gatcgccctt cccaacagtt gcgcagcctg aatggcgaat gcgatttatt      2160
caacaaagcc gccgtcccgt caagtcagcg taatgctctg ccagtgttac aaccaattaa      2220
ccaattctga ttagaaaaac tcatcgagca tcaaatgaaa ctgcaattta ttcatatcag      2280
gattatcaat accatatttt tgaaaagcc gtttctgtaa tgaaggagaa aactcaccga      2340
ggcagttcca taggatggca agatcctggt atcggtctgc gattccgact cgtccaacat      2400
caatacaacc tattaatttc ccctcgtcaa aaataaggtt atcaagtgag aaatcaccat      2460
gagtgacgac tgaatccggt gagaatggca aaagcttatg catttctttc cagacttgtt      2520
caacaggcca gccattacgc tcgtcatcaa aatcactcgc atcaaccaaa ccgttattca      2580
ttcgtgattg cgcctgagcg agacgaaata cgcgatcgct gttaaaagga caattacaaa      2640
caggaatcga atgcaaccgg cgcaggaaca ctgccagcgc atcaacaata ttttcacctg      2700
aatcaggata ttcttctaat acctggaatg ctgttttccc ggggatcgca gtggtgagta      2760
accatgcatc atcaggagta cggataaaat gcttgatggt cggaagaggc ataaattccg      2820
tcgccagttt agtctgacca tctcatctgt aacatcattg gcaacgctac ctttgccatg      2880
tttcagaaac aactctggcg catcgggctt cccatacaat cgatagattg tcgcacctga      2940
ttgcccgaca ttatcgcgag cccatttata cccatataaa tcagcatcca tgttggaatt      3000
taatcgcggc ttcgagcaag acgtttcccg ttgaatatgg ctcataacac cccttgtatt      3060
actgtttatg taagcagaca gttttattgt tcatgatgat atatttttat cttgtgcaat      3120
gtaacatcag agattttgag acacaacgtg gctttgttga ataaatcgaa cttttgctga      3180
gttgaaggat cagatcacgc atcttcccga caacgcagac cgttccgtgg caaagcaaaa      3240
gttcaaaatc accaactggc ccacctacaa caaagctctc atcaaccgtg gctccctcac      3300
tttctggctg gatgatgggg cgattcaggc ctggtatgag tcagcaacac cttcttcacg      3360
aggcagacct c                                                            3371

<210> SEQ ID NO 2
<211> LENGTH: 74
<212> TYPE: DNA
<213> ORGANISM: methancoccus jannaschii

<400> SEQUENCE: 2
ccggcggtag ttcagcctgg tagaacggcg gactgtagat ccgcatgtcg ctggttcaaa      60
tccggcccgc cgga                                                         74

<210> SEQ ID NO 3
<211> LENGTH: 936
<212> TYPE: DNA
<213> ORGANISM: E. coli

<400> SEQUENCE: 3
atggacgaat ttgaaatgat aaagagaaac acatctgaaa ttatcagcga ggaagagtta      60
agagaggttt taaaaaaaga tgaaaaatct gctcaaatag ttttgaacc aagtggtaaa      120 atacatttag ggcattatct ccaaataaaa aagatgattg atttacaaaa tgctggattt      180
gatataatta tattgttggc tgatttacac gcctatttaa accagaaagg agagttggat      240
gagattagaa aataggaga ttataacaaa aaagttttg aagcaatggg gttaaaggca      300
aaatatgttt atgaagtac attccagctt gataaggatt atacactgaa tgtctataga      360
ttggctttaa aaactacctt aaaaagagca agaaggagta tggaacttat agcaagagag      420
```

```
gatgaaaatc caaaggttgc tgaagttatc tatccaataa tgcaggttaa tgctattcat    480
tatccaggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatgagaa tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagacatca ccatcaccat cactta                              936
```

<210> SEQ ID NO 4
<211> LENGTH: 408
<212> TYPE: DNA
<213> ORGANISM: E. coli

<400> SEQUENCE: 4

```
atggcaccag cacgtagtcc tagccccagc acgcagccct gggagcatgt gaatgccatc     60
caggaggccc ggcgtctcct gaacctgagt cgtgacactg ctgctgagat gtaggaaaca    120
gtagaagtca tctcagaaat gttttgacctc caggagccga cctgcttaca gacccgcctg    180
gagctgtaca agcagggcct gcgtggcagc ctcaccaagc tcaagggccc cttgaccatg    240
atggccagcc actacaagca gcactgccct ccaaccccgg aaacttcctg tgcaacccag    300
attatcacct ttgaaagttt caaagagaac ctgaaggact ttctgcttgt catcccttt     360 gactgctggg agccagtcca ggagcatcac catcaccatc actaataa                 408
```

<210> SEQ ID NO 5
<211> LENGTH: 408
<212> TYPE: DNA
<213> ORGANISM: E. coli

<400> SEQUENCE: 5

```
atggcaccag cacgtagtcc tagccccagc acgcagccct gggagcatgt gaatgccatc     60
caggaggccc ggcgtctcct gaacctgagt cgtgacactg ctgctgagat gtaggaaaca    120
gtagaagtca tctcagaaat gttttgacctc caggagccga cctgcttaca gacccgcctg    180
gagctgtaca agcagggcct gcgtggcagc ctcaccaagc tcaagggccc cttgaccatg    240
atggccagcc actacaagca gcactgccct ccaaccccgg aaacttcctg tgcaacccag    300
attatcacct ttgaaagttt caaagagaac ctgaaggact ttctgcttgt catcccttt     360 gactgctggg agccagtcca ggagcatcac catcaccatc actaataa                 408
```

<210> SEQ ID NO 6
<211> LENGTH: 411
<212> TYPE: DNA
<213> ORGANISM: E. coli

<400> SEQUENCE: 6

```
atggcaccaa cacgtagtcc tatcactgtc acccggcctt ggaagcatgt agaggccatc     60
aaagaagccc tgaacctcct ggatgacatg cctgtcacat tgaatgaaga ggtagaagtc    120
gtctctaacg agttctcctt caagaagcta acatgtgtgc agacccgcct gaagatattc    180
gagcagggtc tacggggcaa tttcaccaaa ctcaagggcg ccttgtagat gacagccagc    240
tactaccaga catactgccc cccaactccg gaaacggact gtgaaacaca agttaccacc    300
```

| | |
|---|---|
| tatgcggatt tcatagacag ccttaaaacc tttctgactg atatcccctt tgaatgcaaa | 360 |
| aaaccagtcc aaaaaggagg aggtggccac catcatcacc accattaata a | 411 |

<210> SEQ ID NO 7
<211> LENGTH: 1196
<212> TYPE: DNA
<213> ORGANISM: E. coli

<400> SEQUENCE: 7

| | |
|---|---|
| atgaaatcta acaatgcgct catcgtcatc ctcggcaccg tcaccctgga tgctgtaggc | 60 |
| ataggcttgg ttatgccggt actgccgggc ctcttgcggt agatcgtcca ttccgacagc | 120 |
| atcgccagtc actatggcgt gctgctagcg tatatgcgtt gatgcaattt ctatgcgcac | 180 |
| ccgttctcgg agcactgtcc gaccgctttg gccgccgccc agtcctgctc gcttcgctac | 240 |
| ttggagccac tatcgactac gcgatcatgg cgaccacacc cgtcctgtgg atcctctacg | 300 |
| ccggacgcat cgtggccggc atcaccggcg ccacaggtgc ggttgctggc gcctatatcg | 360 |
| ccgacatcac cgatggggaa gatcgggctc gccacttcgg gctcatgagc gcttgtttcg | 420 |
| gcgtgggtat ggtggcaggc cccgtggccg ggggactgtt gggcgccatc tccttgcatg | 480 |
| caccattcct tgcggcggcg gtgctcaacg gcctcaacct actactgggc tgcttcctaa | 540 |
| tgcaggagtc gcataaggga gagcgtcgac cgatgccctt gagagccttc aacccagtca | 600 |
| gctccttccg gtgggcgcgg ggcatgacta tcgtcgccgc acttatgact gtcttcttta | 660 |
| tcatgcaact cgtaggacag gtgccggcag cgctctgggt cattttcggc gaggaccgct | 720 |
| ttcgctggag cgcgacgatg atcggcctgt cgcttgcggt attcggaatc ttgcacgccc | 780 |
| tcgctcaagc cttcgtcact ggtcccgcca ccaaacgttt cggcgagaag caggccatta | 840 |
| tcgccggcat ggcggccgac gcgctgggct acgtcttgct ggcgttcgcg acgcgaggct | 900 |
| ggatggcctt ccccattatg attcttctcg cttccggcgg catcgggatg cccgcgttgc | 960 |
| aggccatgct gtccaggcag gtagatgacg accatcaggg acagcttcaa ggatcgctcg | 1020 |
| cggctcttac cagcctaact tcgatcactg gaccgctgat cgtcacgcg atttatgccg | 1080 |
| cctcggcgag cacatggaac gggttggcat ggattgtagg cgccgcccta taccttgtct | 1140 |
| gcctccccgc gttgcgtcgc ggtgcatgga gccgggccac ctcgacctga taataa | 1196 |

<210> SEQ ID NO 8
<211> LENGTH: 1197
<212> TYPE: DNA
<213> ORGANISM: E. coli

<400> SEQUENCE: 8

| | |
|---|---|
| atgaaatcta acaatgcgct catcgtcatc ctcggcaccg tcaccctgga tgctgtaggc | 60 |
| ataggcttgg ttatgccggt actgccgggc ctcttgcggt agatcgtcca ttccgacagc | 120 |
| atcgccagtc actatggcgt gctgctagcg ctatatgcgt tgatgcaatt tctatgcgca | 180 |
| cccgttctcg gagcactgtc cgaccgcttt ggccgccgcc cagtcctgct cgcttcgcta | 240 |
| cttggagcca ctatcgacta cgcgatcatg gcgaccacac ccgtcctgtg gatcctctac | 300 |
| gccggacgca tcgtggccgg catcaccggc gccacaggtg cggttgctgg cgcctatatc | 360 |
| gccgacatca ccgatgggga agatcgggct cgccacttcg ggctcatgag cgcttgtttc | 420 |
| ggcgtgggta tggtggcagg ccccgtggcc gggggactgt tgggcgccat ctccttgcat | 480 |
| gcaccattcc ttgcggcggc ggtgctcaac ggcctcaacc tactactggg ctgcttccta | 540 |
| atgtaggagt cgcataaggg agagcgtcga ccgatgccct tgagagcctt caacccagtc | 600 |

```
agctccttcc ggtgggcgcg gggcatgact atcgtcgccg cacttatgac tgtcttcttt      660
atcatgcaac tcgtaggaca ggtgccggca gcgctctggg tcattttcgg cgaggaccgc      720
tttcgctgga gcgcgacgat gatcggcctg tcgcttgcgg tattcggaat cttgcacgcc      780
ctcgctcaag ccttcgtcac tggtcccgcc accaaacgtt tcggcgagaa gcaggccatt      840
atcgccggca tggcggccga cgcgctgggc tacgtcttgc tggcgttcgc gacgcgaggc      900
tggatggcct tccccattat gattcttctc gcttccggcg catcgggat gcccgcgttg       960 caggccatgc tgtccaggca ggtagatgac gaccatcagg acagcttca aggatcgctc      1020 gcggctctta ccagcctaac ttcgatcact ggaccgctga tcgtcacggc gatttatgcc     1080
gcctcggcga gcacatggaa cgggttggca tggattgtag gcgccgccct ataccttgtc     1140
tgcctccccg cgttgcgtcg cggtgcatgg agccgggcca cctcgacctg ataataa       1197
```

```
<210> SEQ ID NO 9
<211> LENGTH: 405
<212> TYPE: DNA
<213> ORGANISM: MS2

<400> SEQUENCE: 9
```

```
catatggcca gcaactttac ccagttcgtt ctggttgaca acggcggtta gggcgacgtg       60
acggtggcgc cgtctaactt cgccaacggt gttgcggagt ggatttcttc taattctcgc      120
agccaagcct ataaagttac gtgttctgtg cgtcagtcta gcgcccagaa tcgcaagtac      180
accattaaag tggaggtgcc gaaggtggcg acgcaaaccg tgggtggtgt ggagctgcca      240
gttgcggcct ggcgtagcta tctgaacatg gagctgacga tcccaatctt tgccaccaat      300
agcgactgcg aactgattgt gaaggccatg caggttctgc tgaaggatgg taacccgatt      360
ccatctgcca ttgccgcgaa ctctggtatc tactaataag tcgac                      405
```

```
<210> SEQ ID NO 10
<211> LENGTH: 74
<212> TYPE: DNA
<213> ORGANISM: methanococcus jannaschii

<400> SEQUENCE: 10
```

```
ccggcggtag ttcagcctgg tagaacggcg gactgtagat ccgcatgtcg ctggttcaaa       60
tccggcccgc cgga                                                         74
```

```
<210> SEQ ID NO 11
<211> LENGTH: 30
<212> TYPE: DNA
<213> ORGANISM: Artificial Sequence
<220> FEATURE:
<223> OTHER INFORMATION: artificial primer

<400> SEQUENCE: 11
```

```
gtggcaatat ggtcgctcag gactggatgg                                        30
```

```
<210> SEQ ID NO 12
<211> LENGTH: 31
<212> TYPE: DNA
<213> ORGANISM: Artificial Sequence
<220> FEATURE:
<223> OTHER INFORMATION: artificial primer

<400> SEQUENCE: 12
```

```
ggtaggtcaa ggactcgctg gtataacggt g                                      31
```

```
<210> SEQ ID NO 13
```

```
<211> LENGTH: 18
<212> TYPE: PRT
<213> ORGANISM: MS2 virus
<220> FEATURE:
<221> NAME/KEY: VARIANT
<222> LOCATION: (8)...(8)
<223> OTHER INFORMATION: azido-phenylalanine
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 8
<223> OTHER INFORMATION: Xaa = Any Amino Acid

<400> SEQUENCE: 13

Val Leu Val Asp Asn Gly Gly Xaa Gly Asp Val Thr Val Ala Pro Ser
 1               5                  10                  15

Asn Phe
```